US012679821B2

(12) United States Patent
Uchida et al.

(10) Patent No.: US 12,679,821 B2
(45) Date of Patent: Jul. 14, 2026

(54) CYCLIC AZINE COMPOUND, MATERIAL FOR ORGANIC LIGHT EMITTING DIODE, ELECTRON TRANSPORT MATERIAL FOR ORGANIC LIGHT EMITTING DIODE, AND ORGANIC LIGHT EMITTING DIODE

(71) Applicants: TOSOH CORPORATION, Shunan (JP); SAGAMI CHEMICAL RESEARCH INSTITUTE, Ayase (JP)

(72) Inventors: Naoki Uchida, Ayase (JP); Hidenori Aihara, Ayase (JP); Takuya Yamagata, Ayase (JP); Naoki Hayakawa, Ayase (JP); Natsumi Nakajima, Ayase (JP); Kazuki Hattori, Ayase (JP); Fuminari Uehara, Ayase (JP); Yohei Ono, Ayase (JP); Masaya Hirano, Ayase (JP); Yuta Morinaka, Ayase (JP); Keisuke Nomura, Ayase (JP); Eriko Ohta, Ayase (JP); Tomohiro Shono, Shunan (JP); Kana Oike, Ayase (JP); Kazushi Hayashi, Ayase (JP); Keiya Aoyagi, Ayase (JP); Kosuke Sato, Ayase (JP); Toshiki Nishiura, Ayase (JP)

(73) Assignees: TOSOH CORPORATION, Shunan (JP); SAGAMI CHEMICAL RESEARCH INSTITUTE, Ayase (JP)

( * ) Notice: Subject to any disclaimer, the term of this patent is extended or adjusted under 35 U.S.C. 154(b) by 1128 days.

(21) Appl. No.: 17/630,859

(22) PCT Filed: Jul. 22, 2020

(86) PCT No.: PCT/JP2020/028488
§ 371 (c)(1),
(2) Date: Jan. 27, 2022

(87) PCT Pub. No.: WO2021/020285
PCT Pub. Date: Feb. 4, 2021

(65) Prior Publication Data

US 2022/0274952 A1 Sep. 1, 2022

(30) Foreign Application Priority Data

Jul. 30, 2019 (JP) ................................ 2019-139746

(51) Int. Cl.
*C07C 255/46* (2006.01)
*C07D 209/86* (2006.01)
(Continued)

(52) U.S. Cl.
CPC .......... *C07D 401/10* (2013.01); *C07C 255/46* (2013.01); *C07D 209/86* (2013.01);
(Continued)

(58) Field of Classification Search
CPC .. C07D 401/10; C07D 209/86; C07D 251/24; C07C 255/46; H10K 85/654
See application file for complete search history.

(56) References Cited

U.S. PATENT DOCUMENTS

2010/0249406 A1* 9/2010 Yamakawa .......... C07D 251/24
544/216
2012/0214993 A1* 8/2012 Aihara .................. H05B 33/10
544/333
(Continued)

FOREIGN PATENT DOCUMENTS

CN 101675038 A 3/2010
JP 2008-280330 A 11/2008
(Continued)

OTHER PUBLICATIONS

WO-2017179809-A1—translation (Year: 2017).*
International Search Report mailed on Oct. 13, 2020 in PCT/JP2020/028488 filed on Jul. 22, 2020 (3 pages).

*Primary Examiner* — Rachel Simbana
(74) *Attorney, Agent, or Firm* — Oblon, McClelland, Maier & Neustadt, L.L.P.

(57) ABSTRACT

An object of the present invention is to provide a cyclic azine compound exhibiting both excellent driving voltage
(Continued)

characteristics and excellent current efficiency characteristics. The desired cyclic azine compound has a specific structure represented by formula (1).

[Chem. 1]

(1)

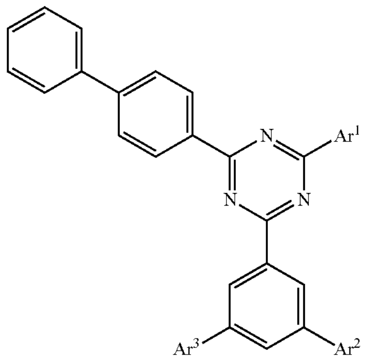

10 Claims, 2 Drawing Sheets

(51) Int. Cl.

| | |
|---|---|
| ***C07D 213/16*** | (2006.01) |
| ***C07D 251/24*** | (2006.01) |
| ***C07D 307/91*** | (2006.01) |
| ***C07D 401/10*** | (2006.01) |
| ***C07D 401/14*** | (2006.01) |
| ***C07D 487/14*** | (2006.01) |
| ***C07F 5/02*** | (2006.01) |
| ***C07F 7/08*** | (2006.01) |
| ***H10K 50/16*** | (2023.01) |
| ***H10K 85/60*** | (2023.01) |

(52) U.S. Cl.

CPC ......... *C07D 251/24* (2013.01); *C07D 307/91* (2013.01); *C07D 401/14* (2013.01); *C07D 487/14* (2013.01); *C07F 5/027* (2013.01); *C07F 7/081* (2013.01); *H10K 50/166* (2023.02); *H10K 85/611* (2023.02); *H10K 85/652* (2023.02); *H10K 85/654* (2023.02); *H10K 85/6572* (2023.02); *H10K 85/6574* (2023.02)

(56) References Cited

U.S. PATENT DOCUMENTS

| | | | |
|---|---|---|---|
| 2012/0313090 | A1 | 12/2012 | Yamakawa et al. |
| 2015/0329544 | A1 | 11/2015 | Aihara et al. |
| 2017/0092871 | A1 | 3/2017 | Kim et al. |

FOREIGN PATENT DOCUMENTS

| | | | | |
|---|---|---|---|---|
| JP | 2009-224512 | A | 10/2009 | |
| JP | 2017-178931 | A | 10/2017 | |
| KR | 10-2015-0120875 | A | 10/2015 | |
| WO | WO 2011/021689 | A1 | 2/2011 | |
| WO | WO-2017179809 | A1 * | 10/2017 | ........... C07D 209/82 |

* cited by examiner

CYCLIC AZINE COMPOUND, MATERIAL FOR ORGANIC LIGHT EMITTING DIODE, ELECTRON TRANSPORT MATERIAL FOR ORGANIC LIGHT EMITTING DIODE, AND ORGANIC LIGHT EMITTING DIODE

CROSS-REFERENCE TO RELATED APPLICATIONS

The present application is a 35 U.S.C. § 371 national stage patent application of International patent application PCT/JP2020/028488, filed on Jul. 22, 2020, which is based on and claims the benefits of priority to Japanese Application No. 2019-139746, filed on Jul. 30, 2019. The entire contents of these applications are incorporated herein by reference.

TECHNICAL FIELD

The present disclosure relates to a cyclic azine compound, a material for an organic light emitting diode, an electron transport material for an organic light emitting diode, and an organic light emitting diode.

BACKGROUND ART

Organic light emitting diodes have been used in applications including not only small-sized displays but also large-sized televisions and lighting fixtures, and have been intensively developed. For example, Patent Document 1 discloses, as a material for an organic light emitting diode, a cyclic azine compound having a specific substituent, the cyclic azine compound serving to provide an organic light emitting diode exhibiting excellent thermal resistance and having low driving voltage and an extended lifetime.

Patent Document 1: Japanese Unexamined Patent Application, Publication No. 2008-280330

DISCLOSURE OF THE INVENTION

Problems to be Solved by the Invention

In recent years, however, market demands for organic light emitting diodes have become increasingly stringent, and there is a need to develop a material exhibiting both excellent driving voltage characteristics and excellent current efficiency characteristics. In this regard, an organic light emitting diode that contains the cyclic azine compound disclosed in Patent Document 1 exhibits excellent long life and current efficiency characteristics, but there is a desire to further improve driving voltage properties.

An aspect of the present disclosure is directed to providing a cyclic azine compound, a material for an organic light emitting diode, and an electron transport material for an organic light emitting diode, which exhibit both excellent driving voltage characteristics and excellent current efficiency characteristics. Furthermore, another aspect of the present disclosure is directed to providing an organic light emitting diode exhibiting both excellent driving voltage characteristics and excellent current efficiency characteristics.

Means for Solving the Problems

According to an aspect of the present disclosure, a cyclic azine compound represented by formula (1) is provided,

[Chem. 1]

(1)

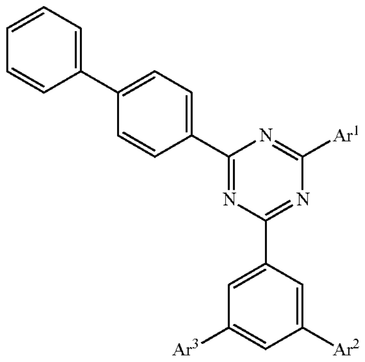

wherein in the formula (1), $Ar^1$ represents a phenyl group or a 4-biphenylyl group;

$Ar^2$ represents any one of groups represented by formulas (2-1) to (2-3):

[Chem. 2]

(2-1)

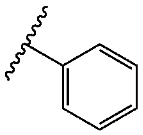

(2-2)

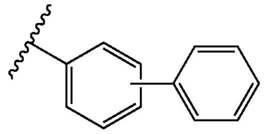

(2-3)

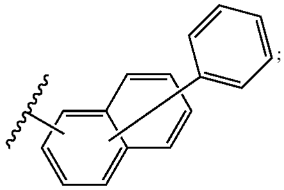

;

and $Ar^3$ represents a group represented by formula (3):

[Chem. 3]

(3)

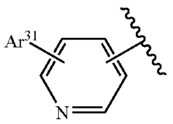

wherein in the formula (3), $Ar^{31}$ represents:

a hydrogen atom, or a group represented by any one of the formulas (2-1) to (2-3).

According to another aspect of the present disclosure, a material for an organic light emitting diode which contains the cyclic azine compound described above is provided.

According to another aspect of the present disclosure, an electron transport material for an organic light emitting diode which contains the cyclic azine compound described above is provided. According to another aspect of the present disclosure, an organic light emitting diode containing the cyclic azine compound described above is provided.

Effects of the Invention

According to an aspect of the present disclosure, a cyclic azine compound, a material for an organic light emitting diode, and an electron transport material for an organic light emitting diode, which exhibit both excellent driving voltage characteristics and excellent current efficiency characteristics, are provided. According to another aspect of the present disclosure, an organic light emitting diode exhibiting both excellent driving voltage characteristics and excellent current efficiency characteristics is provided.

PREFERRED MODE FOR CARRYING OUT THE INVENTION

Figure 1:
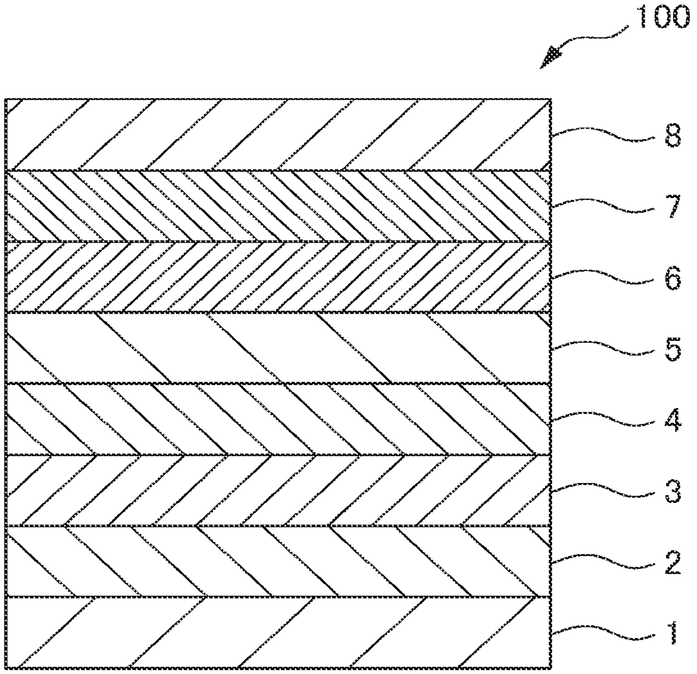
FIG. 1 is a schematic cross-sectional view showing an example of a layered structure of an organic light emitting diode containing a cyclic azine compound according to an aspect of the present disclosure.

Hereinafter, a cyclic azine compound according to an aspect of the present disclosure will be described in detail.

<Cyclic Azine Compound>

A cyclic azine compound according to an aspect of the present disclosure is represented by formula (1):

[Chem. 4]

(1)

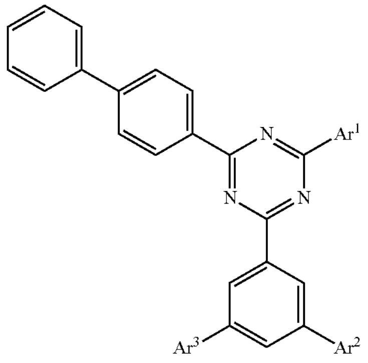

wherein in the formula (1), $Ar^1$ represents a phenyl group or a 4-biphenylyl group;

$Ar^2$ represents a group represented by any one of formulas (2-1) to (2-3):

[Chem. 5]

(2-1)

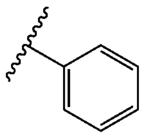

(2-2)

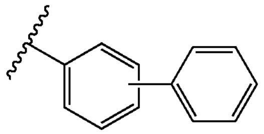

(2-3)

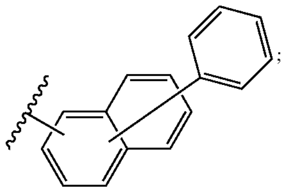

;

and $Ar^3$ represents a group represented by formula (3):

[Chem. 6]

(3)

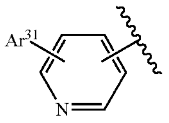

wherein in the formula (3), $Ar^{31}$ represents:

a hydrogen atom, or a group represented by any one of the formulas (2-1) to (2-3).

Hereinafter, the cyclic azine compound represented by the formula (1) may be referred to as a cyclic azine compound (1). The definition of a substituent in the cyclic azine compound (1), and preferred specific examples of the substituent are each as follows.

[$Ar^2$]

$Ar^2$ represents a group represented by any one of the formulas (2-1) to (2-3).

[Chem. 7]

(2-1)

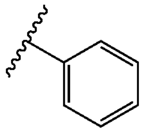

(2-2)

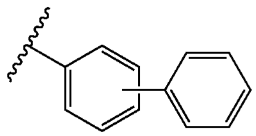

-continued (2-3)

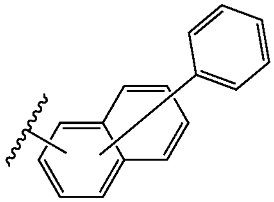

More preferably, $Ar^2$ represents a group represented by formula (2-1), (2-2a), (2-2b), (2-3a), or (2-3b) from the viewpoint of the achievement of both excellent driving voltage characteristics and excellent current efficiency characteristics.

[Chem. 8]

(2-1)

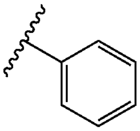

(2-2a)

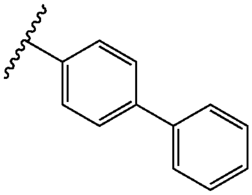

(2-2b)

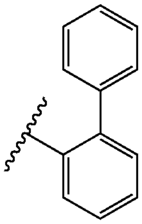

(2-3a)

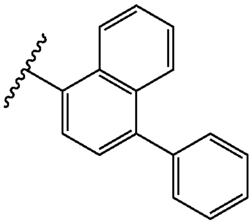

(2-3b)

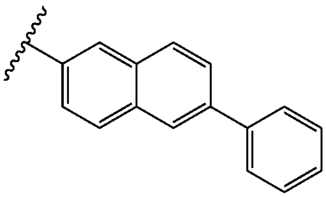

[$Ar^3$]

$Ar^3$ represents a group represented by formula (3):

[Chem. 9]

(3)

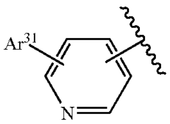

wherein $Ar^{31}$ represents:

a hydrogen atom, or a group represented by any one of the formulas (2-1) to (2-3).

Preferably, $Ar^3$ represents a group represented by any one of formulas (3-1) to (3-9) from the viewpoint of the achievement of both excellent driving voltage characteristics and excellent current efficiency characteristics.

[Chem. 10]

(3-1)

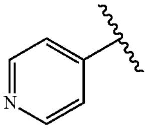

(3-2)

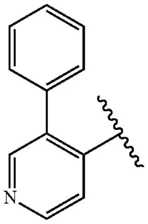

(3-3)

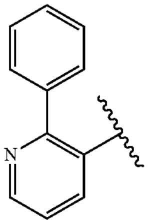

(3-4)

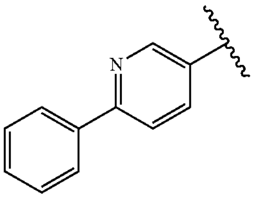

(3-5)

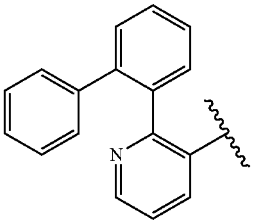

-continued (3-6)

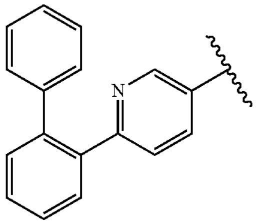

(3-7)

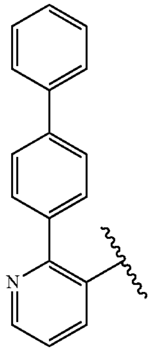

(3-8)

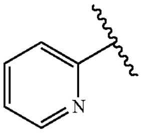

(3-9)

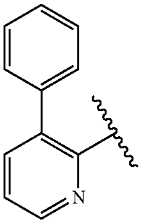

The cyclic azine compound (1), when used as a part of constitutive components of an organic light emitting diode (OLED), exerts the effects of achieving a high current efficiency, a low driving voltage, and the like. In particular, when the cyclic azine compound (1) is used as an electron transport layer, these effects are even further significant.

[Preferable Examples of Cyclic Azine Compound (1)]

Each cyclic azine compound represented by any one of the compounds (1-1) to (1-90), which are specified in Tables 1 to 3, is more preferable from the viewpoint of the achievement of both excellent driving voltage characteristics and excellent current efficiency characteristics.

TABLE 1

| | Structure of cyclic azine compound (1) | | |
|---|---|---|---|
| Compound | $Ar^1$ | $Ar^2$ | $Ar^3$ |
| (1-1) | Phenyl | (2-1) | (3-1) |
| (1-2) | Phenyl | (2-1) | (3-2) |
| (1-3) | Phenyl | (2-1) | (3-3) |
| (1-4) | Phenyl | (2-1) | (3-4) |
| (1-5) | Phenyl | (2-1) | (3-5) |
| (1-6) | Phenyl | (2-1) | (3-6) |
| (1-7) | Phenyl | (2-1) | (3-7) |
| (1-8) | Phenyl | (2-1) | (3-8) |
| (1-9) | Phenyl | (2-1) | (3-9) |
| (1-10) | Phenyl | (2-2a) | (3-1) |
| (1-11) | Phenyl | (2-2a) | (3-2) |
| (1-12) | Phenyl | (2-2a) | (3-3) |
| (1-13) | Phenyl | (2-2a) | (3-4) |
| (1-14) | Phenyl | (2-2a) | (3-5) |
| (1-15) | Phenyl | (2-2a) | (3-6) |
| (1-16) | Phenyl | (2-2a) | (3-7) |
| (1-17) | Phenyl | (2-2a) | (3-8) |
| (1-18) | Phenyl | (2-2a) | (3-9) |
| (1-19) | Phenyl | (2-2b) | (3-1) |
| (1-20) | Phenyl | (2-2b) | (3-2) |
| (1-21) | Phenyl | (2-2b) | (3-3) |
| (1-22) | Phenyl | (2-2b) | (3-4) |
| (1-23) | Phenyl | (2-2b) | (3-5) |
| (1-24) | Phenyl | (2-2b) | (3-6) |
| (1-25) | Phenyl | (2-2b) | (3-7) |
| (1-26) | Phenyl | (2-2b) | (3-8) |
| (1-27) | Phenyl | (2-2b) | (3-9) |
| (1-28) | Phenyl | (2-3a) | (3-1) |
| (1-29) | Phenyl | (2-3a) | (3-2) |
| (1-30) | Phenyl | (2-3a) | (3-3) |

TABLE 2

| | Structure of cyclic azine compound (1) | | |
|---|---|---|---|
| Compound | $Ar^1$ | $Ar^2$ | $Ar^3$ |
| (1-31) | Phenyl | (2-3a) | (3-4) |
| (1-32) | Phenyl | (2-3a) | (3-5) |
| (1-33) | Phenyl | (2-3a) | (3-6) |
| (1-34) | Phenyl | (2-3a) | (3-7) |
| (1-35) | Phenyl | (2-3a) | (3-8) |
| (1-36) | Phenyl | (2-3a) | (3-9) |
| (1-37) | Phenyl | (2-3b) | (3-1) |
| (1-38) | Phenyl | (2-3b) | (3-2) |
| (1-39) | Phenyl | (2-3b) | (3-3) |
| (1-40) | Phenyl | (2-3b) | (3-4) |
| (1-41) | Phenyl | (2-3b) | (3-5) |
| (1-42) | Phenyl | (2-3b) | (3-6) |
| (1-43) | Phenyl | (2-3b) | (3-7) |
| (1-44) | Phenyl | (2-3b) | (3-8) |
| (1-45) | Phenyl | (2-3b) | (3-9) |
| (1-46) | 4-Biphenylyl | (2-1) | (3-1) |
| (1-47) | 4-Biphenylyl | (2-1) | (3-2) |
| (1-48) | 4-Biphenylyl | (2-1) | (3-3) |
| (1-49) | 4-Biphenylyl | (2-1) | (3-4) |
| (1-50) | 4-Biphenylyl | (2-1) | (3-5) |
| (1-51) | 4-Biphenylyl | (2-1) | (3-6) |
| (1-52) | 4-Biphenylyl | (2-1) | (3-7) |
| (1-53) | 4-Biphenylyl | (2-1) | (3-8) |
| (1-54) | 4-Biphenylyl | (2-1) | (3-9) |
| (1-55) | 4-Biphenylyl | (2-2a) | (3-1) |
| (1-56) | 4-Biphenylyl | (2-2a) | (3-2) |
| (1-57) | 4-Biphenylyl | (2-2a) | (3-3) |
| (1-58) | 4-Biphenylyl | (2-2a) | (3-4) |
| (1-59) | 4-Biphenylyl | (2-2a) | (3-5) |
| (1-60) | 4-Biphenylyl | (2-2a) | (3-6) |

TABLE 3

| | Structure of cyclic azine compound (1) | | |
|---|---|---|---|
| Compound | $Ar^1$ | $Ar^2$ | $Ar^3$ |
| (1-61) | 4-Biphenylyl | (2-2a) | (3-7) |
| (1-62) | 4-Biphenylyl | (2-2a) | (3-8) |
| (1-63) | 4-Biphenylyl | (2-2a) | (3-9) |
| (1-64) | 4-Biphenylyl | (2-2b) | (3-1) |
| (1-65) | 4-Biphenylyl | (2-2b) | (3-2) |
| (1-66) | 4-Biphenylyl | (2-2b) | (3-3) |

TABLE 3-continued

| | Structure of cyclic azine compound (1) | | |
|---|---|---|---|
| Compound | $Ar^1$ | $Ar^2$ | $Ar^3$ |
| (1-67) | 4-Biphenylyl | (2-2b) | (3-4) |
| (1-68) | 4-Biphenylyl | (2-2b) | (3-5) |
| (1-69) | 4-Biphenylyl | (2-2b) | (3-6) |
| (1-70) | 4-Biphenylyl | (2-2b) | (3-7) |
| (1-71) | 4-Biphenylyl | (2-2b) | (3-8) |
| (1-72) | 4-Biphenylyl | (2-2b) | (3-9) |
| (1-73) | 4-Biphenylyl | (2-3a) | (3-1) |
| (1-74) | 4-Biphenylyl | (2-3a) | (3-2) |
| (1-75) | 4-Biphenylyl | (2-3a) | (3-3) |
| (1-76) | 4-Biphenylyl | (2-3a) | (3-4) |
| (1-77) | 4-Biphenylyl | (2-3a) | (3-5) |
| (1-78) | 4-Biphenylyl | (2-3a) | (3-6) |
| (1-79) | 4-Biphenylyl | (2-3a) | (3-7) |
| (1-80) | 4-Biphenylyl | (2-3a) | (3-8) |
| (1-81) | 4-Biphenylyl | (2-3a) | (3-9) |
| (1-82) | 4-Biphenylyl | (2-3b) | (3-1) |
| (1-83) | 4-Biphenylyl | (2-3b) | (3-2) |
| (1-84) | 4-Biphenylyl | (2-3b) | (3-3) |
| (1-85) | 4-Biphenylyl | (2-3b) | (3-4) |
| (1-86) | 4-Biphenylyl | (2-3b) | (3-5) |
| (1-87) | 4-Biphenylyl | (2-3b) | (3-6) |
| (1-88) | 4-Biphenylyl | (2-3b) | (3-7) |
| (1-89) | 4-Biphenylyl | (2-3b) | (3-8) |
| (1-90) | 4-Biphenylyl | (2-3b) | (3-9) |

Among the cyclic azine compounds specified in Tables 1 to 3, a cyclic azine compound represented by formula (1-6), (1-15), (1-48), (1-49), (1-51), (1-52), (1-54), (1-64), (1-65), (1-66), (1-67), (1-71), (1-73) or (1-82) are preferable in that a light emitting diode exhibiting both particularly excellent driving voltage characteristics and particularly excellent current efficiency characteristics is provided.

[Chem. 11]

1-6

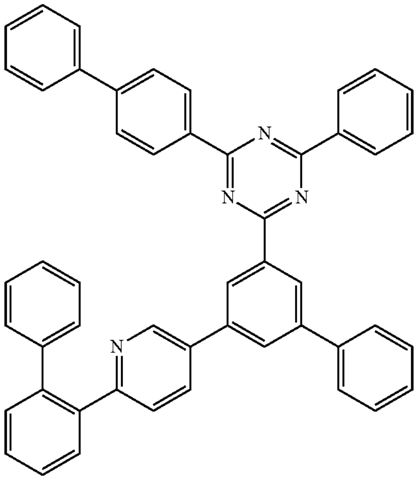

-continued 1-15

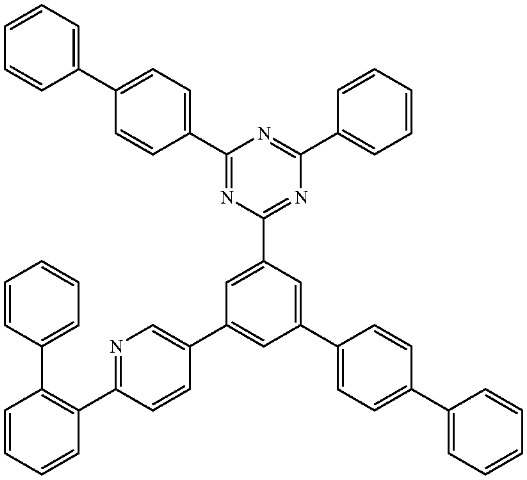

1-48

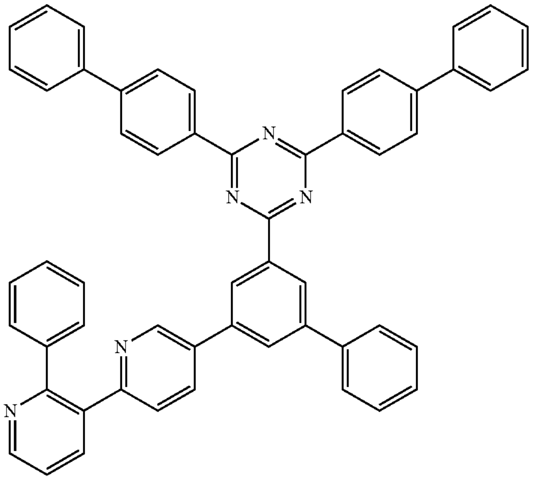

1-49

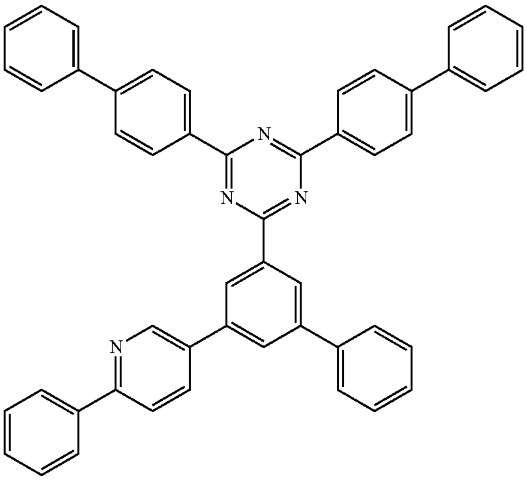

-continued
1-51
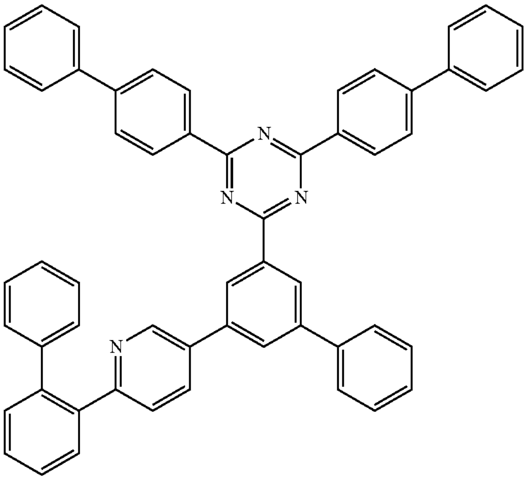
1-52
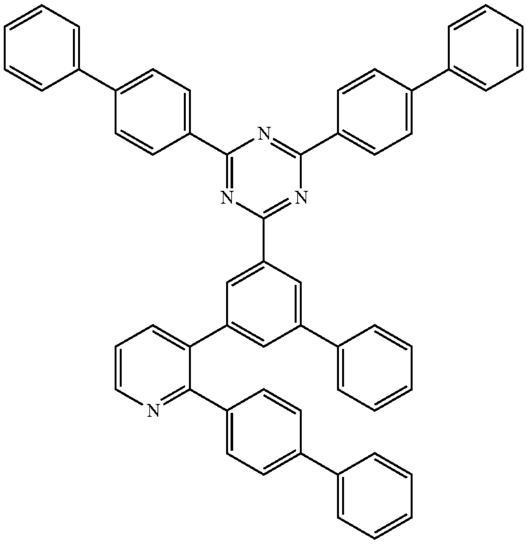
1-54
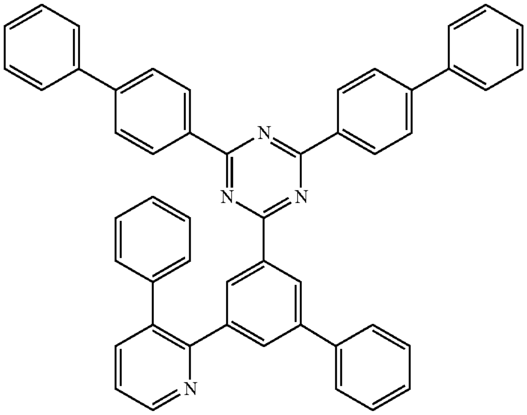
-continued
1-71
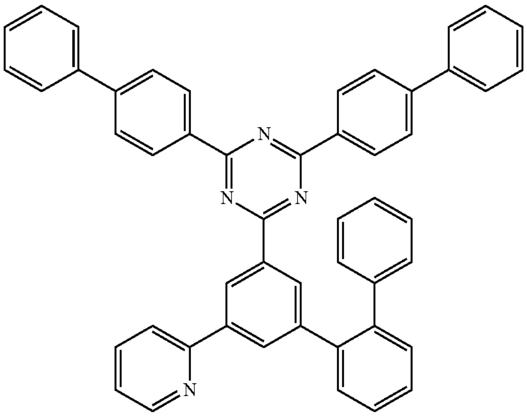
1-64
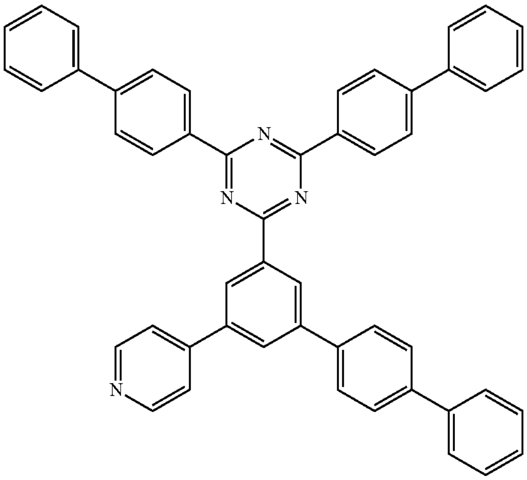
1-65
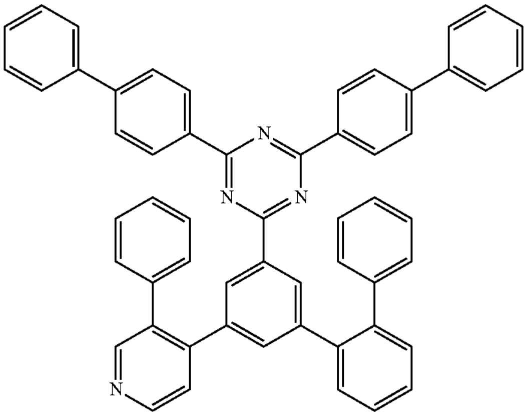

-continued 1-66

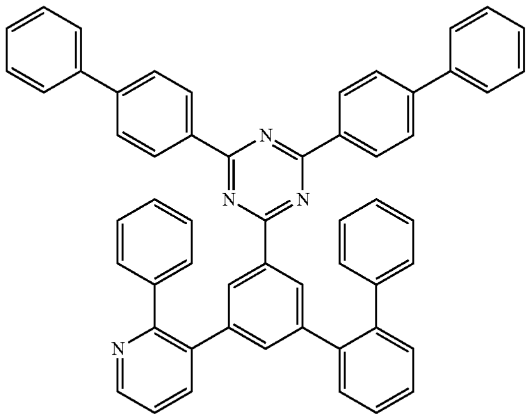

1-67

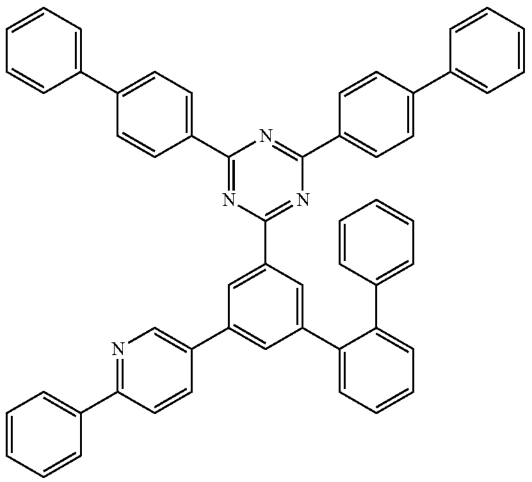

1-73

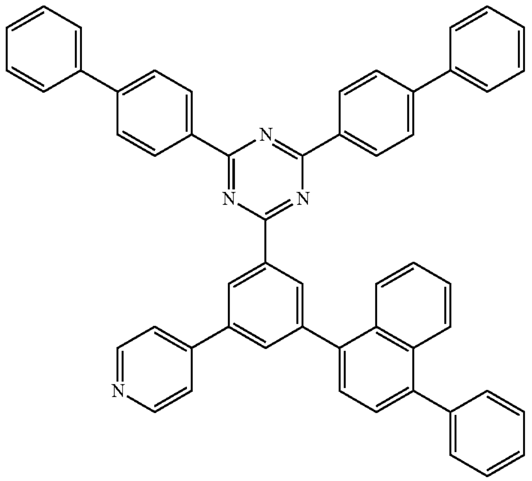

-continued 1-82

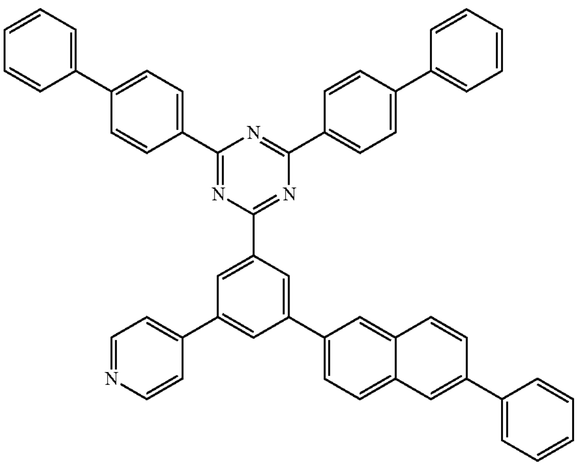

Hereinafter, applications of the cyclic azine compound (1) will be described.

<Material for Organic Light Emitting Diode, and Electron Transport Material for Organic Light Emitting Diode>

The cyclic azine compound (1) may be used, for example, as a material for an organic light emitting diode, although the applications of the cyclic azine compound (1) are not particularly limited thereto. In addition, the cyclic azine compound (1) may be used, for example, as an electron transport material for an organic light emitting diode.

Specifically, a material for an organic light emitting diode according to an aspect of the present disclosure contains the cyclic azine compound (1). Further, an electron transport material for an organic light emitting diode according to an aspect of the present disclosure contains the cyclic azine compound (1). The material for an organic light emitting diode and the electron transport material for an organic light emitting diode, which contain the cyclic azine compound (1), contribute to the manufacture of an organic light emitting diode exhibiting both excellent driving voltage characteristics and excellent current efficiency characteristics.

<Organic Light Emitting Diode>

An organic light emitting diode according to an aspect of the present disclosure contains the cyclic azine compound (1). Although the configuration of the organic light emitting diode is not particularly limited, examples thereof include configurations (i) to (vii) described below.

(i): anode/light emitting layer/cathode (ii): anode/hole transport layer/light emitting layer/cathode (iii): anode/light emitting layer/electron transport layer/cathode (iv): anode/hole transport layer/light emitting layer/electron transport layer/cathode (v): anode/hole injection layer/hole transport layer/light emitting layer/electron transport layer/electron injection layer/cathode (vi): anode/hole injection layer/charge generation layer/hole transport layer/light emitting layer/electron transport layer/cathode (vii): anode/hole injection layer/hole transport layer/electron blocking layer/light emitting layer/hole blocking layer/electron transport layer/electron injection layer/cathode Hereinafter, the organic light emitting diode according to an aspect of the present disclosure will be described in more detail with reference to FIG. 1 using the configuration (vi) shown above as an example. FIG. 1 is a schematic cross-sectional view showing an example of a layered structure of the organic light emitting diode containing the cyclic azine compound according to an aspect of the present disclosure.

It should be noted that, although the organic electroluminescence element shown in FIG. 1 has an element configuration of the so-called bottom-emission type, the organic electroluminescence element according to an aspect of the present disclosure is not limited to those having the element configuration of the bottom-emission type. In other words, the organic electroluminescence element according to an aspect of the present disclosure may have an element configuration of the top-emission type, or another known element configuration.

An organic light emitting diode 100 includes a substrate 1, an anode 2, a hole injection layer 3, a charge generation layer 4, a hole transport layer 5, a light emitting layer 6, an electron transport layer 7, and a cathode 8 in this order. However, some of these layers may be omitted, and, to the contrary, another layer may be added. For example, an electron injection layer may be provided between the electron transport layer 7 and the cathode 8; or the charge generation layer 4 may be omitted, and the hole transport layer 5 is provided directly on the hole injection layer 3.

Further, a configuration may be employed in which a single layer that combines functions exhibited by a plurality of layers, such as, for example, an electron injection and transport layer that combines the function of the electron injection layer and the function of the electron transport layer in a single layer, is provided in place of the plurality of layers. Furthermore, for example, the single layer of the hole transport layer 5, and the single layer of the electron transport layer 7 may be replaced by a plurality of hole transport layers and a plurality of electron transport layers, respectively.

[Layer Containing Cyclic Azine Compound Represented by Formula (1)]

The organic light emitting diode contains the cyclic azine compound represented by the formula (1) in the light emitting layer, and in one or more layers selected from the group consisting of the layers located between the light emitting layer and the cathode. Therefore, in the exemplary configuration shown in FIG. 1, the organic light emitting diode 100 contains the cyclic azine compound (1) in at least one layer selected from the group consisting of the light emitting layer 6 and the electron transport layer 7. In particular, it is preferable that the electron transport layer 7 contains the cyclic azine compound (1).

It should be noted that the cyclic azine compound (1) may be contained in a plurality of layers included in the organic light emitting diode, and when the electron injection layer is provided between the electron transport layer and the cathode, the electron injection layer may contain the cyclic azine compound (1). In the following, an organic light emitting diode 100 in which the electron transport layer 7 contains the cyclic azine compound (1) will be described.

[Substrate 1]

The substrate is not particularly limited, and examples thereof include a glass plate, a quartz plate, a plastic plate, and the like. In addition, when in the case of a configuration in which the emitted light is extracted from the substrate 1 side, the substrate 1 is transparent with respect to the wavelength of the light.

Examples of an optically transparent plastic film include films made from polyethylene terephthalate (PET), polyethylene naphthalate (PEN), polyether sulfone (PES), polyether imide, polyether ether ketone, polyphenylene sulfide, polyarylate, polyimide, polycarbonate (PC), cellulose triacetate (TAC), cellulose acetate propionate (CAP), and the like.

[Anode 2]

The anode 2 is provided on the substrate 1 (on the hole injection layer 3 side). In the case of an organic light emitting diode configured such that the emitted light is extracted through the anode, the anode is formed from a material that passes or substantially passes the emitted light.

A transparent material which may be used for the anode is not particularly limited, and examples thereof include indium tin oxide (ITO), indium zinc oxide (IZO), tin oxide, aluminum-doped tin oxide, magnesium indium oxide, nickel tungsten oxide, and other metal oxides, metal nitrides such as gallium nitride, metal selenides such as zinc selenide, metal sulfides such as zinc sulfide, and the like.

It should be noted that in the case of an organic light emitting diode configured such that the light is extracted from the cathode side only, the light transmission property of the anode is not important. Therefore, examples of a material which may be used for the anode in this case include gold, iridium, molybdenum, palladium, platinum, and the like. A buffer layer (electrode interface layer) may be provided on the anode.

[Hole Injection Layer 3, and Hole Transport Layer 5]

The hole injection layer 3, the charge generation layer 4 as described later, and the hole transport layer 5 are provided between the anode 2 and the light emitting layer 6 as described later, in the recited order from the anode 2 side. The hole injection layer and the hole transport layer function to transmit holes injected from the anode to the light emitting layer, and the presence of the hole injection layer and the hole transport layer between the anode and the light emitting layer enables more holes to be injected to the light emitting layer at a lower electric field.

In addition, the hole injection layer and the hole transport layer also function as an electron barrier layer. More specifically, electrons injected from the cathode and transported from the electron injection layer and/or the electron transport layer to the light emitting layer are inhibited from leaking into the hole injection layer and/or the hole transport layer by a barrier present in the interface between the light emitting layer and hole injection layer and/or the hole transport layer. Consequently, the electrons are accumulated in the interface on the light emitting layer, which exerts effects such as an improvement in current efficiency, leading to the formation of an organic light emitting diode with excellent light emitting performance.

A material for the hole injection layer and/or the hole transport layer has at least one of the following: hole injection properties, hole transporting properties, and electron barrier properties. The material for the hole injection layer and/or the hole transport layer may be either organic or inorganic.

Specific examples of the material for the hole injection layer and/or the hole transport layer include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, electroconductive high-molecular weight oligomers (thiophene oligomers, in particular), porphyrin compounds, aromatic tertiary amine compounds, styrylamine compounds, and the like. Of these, porphyrin compounds, aromatic tertiary amine compounds and styrylamine compounds are preferable, and aromatic tertiary amine compounds are particularly preferable.

Specific examples of the aromatic tertiary amine compounds and the styrylamine compounds include N,N,N',N'-tetraphenyl-4,4'-diaminophenyl, N,N'-diphenyl-N,N'-bis(3-methylphenyl)-[1,1'-biphenyl]-4,4'-diamine (TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenyl ether, 4,4'-bis(diphenylamino)quadriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostilbenezene, N-phenylcarbazole, 4,4'-bis[N-(1-naphthyl)-N-phenylamino]biphenyl (NPD), 4,4',4"-tris[N-(3-methylphenyl)-N-phenylamino]triphenylamine (MTDATA), and the like. In addition, inorganic compounds such as p-type Si and p-type SiC may be mentioned as an example of the material for the hole injection layer and the material for the hole transport layer.

The hole injection layer and the hole transport layer may each have a single-layer structure formed from one or two or more materials, or a layered structure formed of a plurality of layers having the same composition or different compositions.

[Charge Generation Layer 4]

The charge generation layer 4 may be provided between the hole injection layer 3 and hole transport layer 5. A material of the charge generation layer is not particularly limited, and examples thereof include dipyrazino[2,3-f:2',3'-h]quinoxaline-2,3,6,7,10,11-hexacarbonitrile (HAT-CN). The charge generation layer may have a single-layer structure formed from one or two or more materials, or a layered structure formed of a plurality of layers having the same composition or different compositions.

[Light Emitting Layer 6]

The light emitting layer 6 is provided between the hole transport layer 5 and the electron transport layer 7 as described later. Examples of a material of the light emitting layer include phosphorescent light emitting materials, fluorescent light emitting materials, and thermally activated delayed fluorescent light emitting materials. In the light emitting layer, recombination of an electron-hole pair occurs, resulting in light emission.

The light emitting layer may be formed from a single low-molecular-weight material or a single polymer material, but more generally, the light emitting layer is formed from a host material doped with a guest compound. The light is primarily emitted from a dopant, and may exhibit any color.

Examples of the host material include compounds having a biphenyl group, a fluorenyl group, a triphenylsilyl group, a carbazole group, a pyrenyl group, or an anthryl group. More specifically, DPVBi (4,4'-bis(2,2-diphenylvinyl)-1,1'-biphenyl), BCzVBi (4,4'-bis(9-ethyl-3-carbazovinylene)-1,1'-biphenyl), TBADN (2-tert-butyl-9,10-di(2-naphthyl)anthracene), ADN (9,10-di(2-naphthyl)anthracene), CBP (4,4'-bis(carbazol-9-yl)biphenyl), CDBP (4,4'-bis(carbazol-9-yl)-2,2'-dimethylbiphenyl), 2-(9-phenylcarbazol-3-yl)-9-[4-(4-phenylphenylquinazolin-2-yl)carbazole, 9,10-bis(biphenyl)anthracene, and the like.

Examples of a fluorescent dopant include anthracene, pyrene, tetracene, xanthene, perylene, rubrene, coumarin, rhodamine, quinacridone, dicyanomethylenepyran compounds, thiopyran compounds, polymethine compound, pyrylium, thiapyrylium compounds, fluorene derivative, periflanthene derivatives, indenoperylene derivatives, bis(azinyl)amine boron compounds, bis(azinyl)methane compounds, carbostyryl compounds, and the like. The fluorescent dopant may be a combination of two or more selected from the above-listed materials.

Examples of a phosphorescent dopant include metal complexes such as iridium complexes, platinum complexes, palladium complexes, and osmium complexes.

Specific examples of the fluorescent dopant and the phosphorescent dopant include Alq3 (tris(8-hydroxyquinolinolato)aluminum), DPAVBi (4,4'-bis[4-(di-p-tolylamino)styryl]biphenyl), perylene, bis[2-(4-n-hexylphenyl)quinoline](acetylacetonato)iridium(III), $Ir(PPy)_3$(tris(2-phenylpyridine)iridium(III)), and FIrPic (bis(3,5-difluoro-2-(2-pyridyl)phenyl-(2-carboxypyridyl)iridium(III))), and the like.

The thermally activated delayed fluorescent light emitting material can be used as any of the host material and the guest material as described above. Alternatively, the thermally activated delayed fluorescent light emitting material may emit no light by itself and serve to efficiently transfer an excitation energy to the fluorescent dopant that forms the light emitting layer together with the thermally activated delayed fluorescent light emitting material.

Specific examples of the thermally activated delayed fluorescent light emitting material include 4Cz-IPN (2,4,5,6-tetra(9-carbazolyl)-isophthalonitrile), 5Cz-BN (2,3,4,5,6-penta(9-carbazolyl)-benzonitrile), DACTII (2-[3,6-bis(diphenylamino)carbazol-9-ylphenyl]-4,6-diphenyl-1,3,5-triazine), and the like.

Further, the layer which may contain the light emitting material is not limited to the light emitting layer. For example, a layer adjacent to the light emitting layer (the hole transport layer 5, or the electron transport layer 7) may contain the light emitting material. This allows for further enhancement of the current efficiency of the organic light emitting diode.

The light emitting layer may have a single-layer structure formed from one or two or more materials, or a layered structure formed of a plurality of layers having the same composition or different compositions.

[Electron Transport Layer 7]

The electron transport layer 7 is provided between the light emitting layer 6 and the cathode 8 as described later. The electron transport layer functions to transmit electrons injected from the cathode to the light emitting layer. The presence of the electron transport layer between the cathode and the light emitting layer enables the electrons to be injected into the light emitting layer at a lower electric field.

The electron transport layer preferably contains the cyclic azine compound represented by the formula (1), as described above.

The electron transport layer may further contain a conventionally known electron transport material in addition to the cyclic azine compound (1). Examples of the conventionally known electron transport material include 8-hydroxyquinolinolatolithium (Liq), bis(8-hydroxyquinolinolato)zinc, bis(8-hydroxyquinolinolato)copper, bis(8-hydroxyquinolinolato)manganese, tris(8-hydroxyquinolinolato)aluminum, tris(2-methyl-8-hydroxyquinolinolato)aluminum, tris(8-hydroxyquinolinolato)gallium, bis(10-hydroxybenzo[h]

quinolinolato)beryllium, bis(10-hydroxybenzo[h]quinolinolato)zinc, bis(2-methyl-8-quinolinolato)chlorogallium, bis (2-methyl-8-quinolinolato) (o-cresolato)gallium, bis(2-methyl-8-quinolinolato)-1-naphtholatoaluminum, or bis(2-methyl-8-quinolinolato)-2-naphtholatogallium, 2-[3-(9-phenanthrenyl)-5-(3-pyridinyl)phenyl]-4,6-diphenyl-1,3,5-triazine, and 2-(4,"-di-2-pyridinyl[1,1':3',1"-terphenyl]-5-yl)-4,6-diphenyl-1,3,5-triazine, BCP (2,9-dimethyl-4,7-diphenyl-1,10-phenanthroline), Bphen (4,7-diphenyl-1,10-phenanthroline), BAlq (bis(2-methyl-8-quinolinolato)-4-(phenylphenolato)aluminum), and bis(10-hydroxybenzo[h] quinolinolato)beryllium), and the like.

The electron transport layer may have a single-layer structure formed from one or two or more materials, or a layered structure formed of a plurality of layers having the same composition or different compositions. In the case where the electron transport layer has a two-layer structure including a first electron transport layer on the light emitting layer side and a second electron transport layer on the cathode side, it is preferable that the second electron transport layer contains the cyclic azine compound (1).

[Cathode 8]

The cathode 8 is provided on the electron transport layer 7. In the case of an organic electroluminescence element configured such that only the emitted light having passed through the anode is extracted, the cathode may be formed from any electrically-conductive material. Examples of a material of the cathode include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, rare earth metals, and the like. A buffer layer (electrode interface layer) may be provided on the cathode (on the electron transport layer side thereof).

[Forming Method of Each Layer]

The layers as described above except for the electrodes (the anode and the cathode) may be each formed by making a thin film of the material of each layer (together with a material such as a binder resin, and a solvent, as required) by a known method such as, for example, a vacuum deposition method, a spin coating method, a casting method, or an LB method (Langmuir-Blodgett method). The thickness of each layer formed thus is not particularly limited, and may be appropriately selected according to applications. The thickness of each layer is typically in the range of 5 nm to 5 μm.

The anode and the cathode may be formed by making a thin film of an electrode material by a technique such as vapor deposition or sputtering. A pattern may be formed using a mask having a desired shape during the vapor deposition or sputtering, and a pattern with a desired shape may be formed by photolithography after the formation of a thin film by the vapor deposition or sputtering, etc.

The anode and the cathode each have a thickness of preferably 1 μm or less, and more preferably 10 nm or more and 200 nm or less.

The organic light emitting diode according to an aspect of the present disclosure may be used as a type of lamp such as an illumination lamp and an exposure light source, or as a projection apparatus of the type to project an image or a display device (display) of the type for a viewer to directly view a static image and/or a video. In the case of the use as a display device to play a video, the drive system may be either simple matrix (passive matrix) system or an active matrix system. Further, two or more organic light emitting diodes according to the present aspect which have different emission colors may be used to produce a full-color display device.

It should be noted that the cyclic azine compound (1) according to an aspect of the present disclosure synthesized by an appropriate combination of known reactions (for example, Suzuki-Miyaura cross-coupling reaction, etc.). For example, the cyclic azine compound (1) according to an aspect of the present disclosure can be synthesized according to a production method shown in any one of the reaction formulas (a) to (f) described below, but these examples are in no way to be construed as limiting the present invention.

Scheme (a)

[Chem. 12]

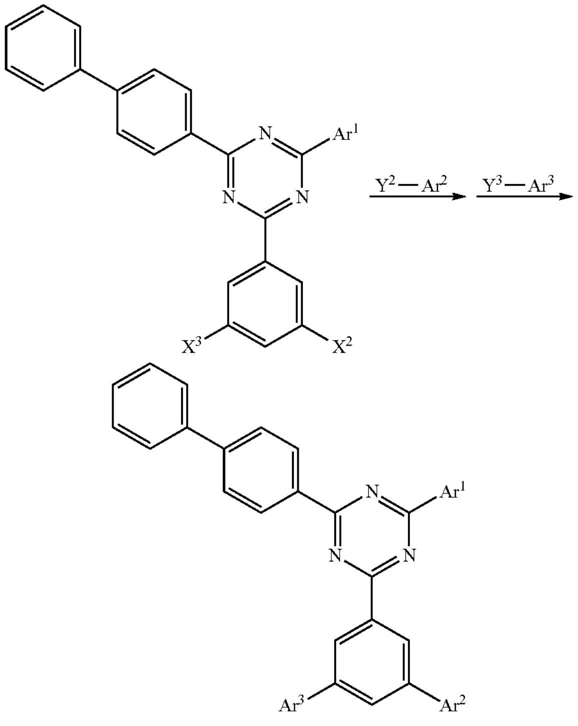

(1)

Scheme (b)

[Chem. 13]

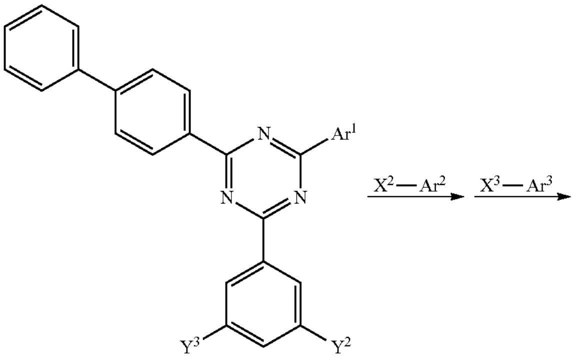

-continued
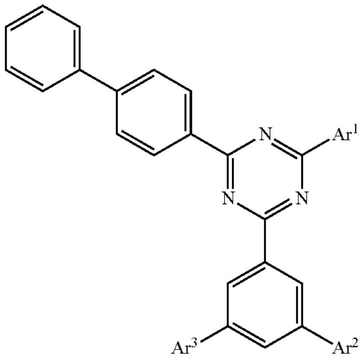
(1)
Scheme (c)
[Chem. 14]
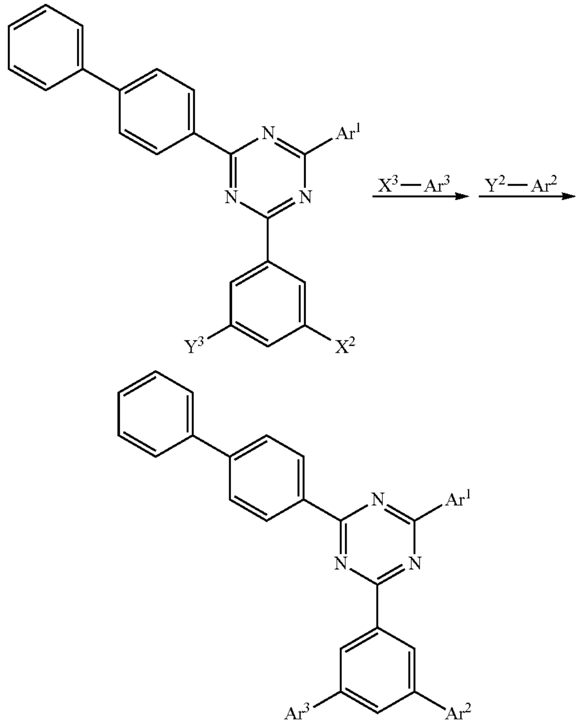
(1)
Scheme (d)
[Chem. 15]
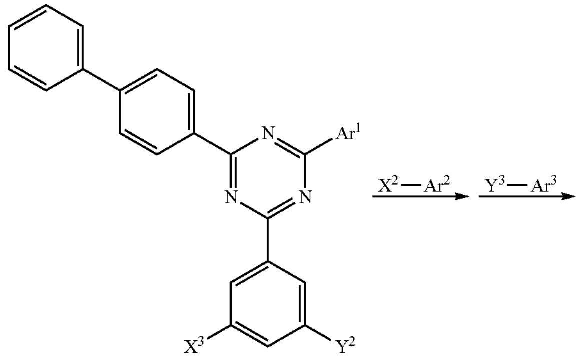
-continued
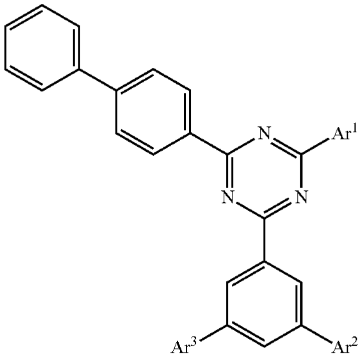
(1)
Scheme (e)
[Chem. 16]
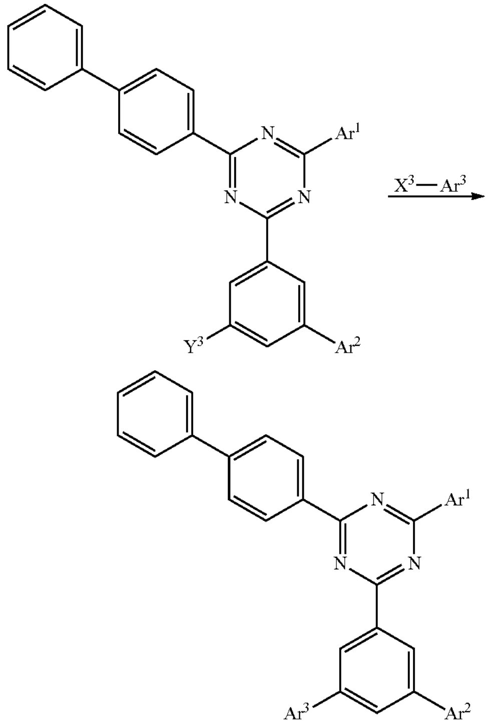
(1)
Scheme (f)
[Chem. 17]
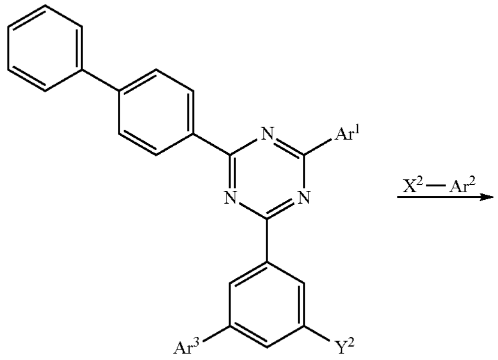

-continued

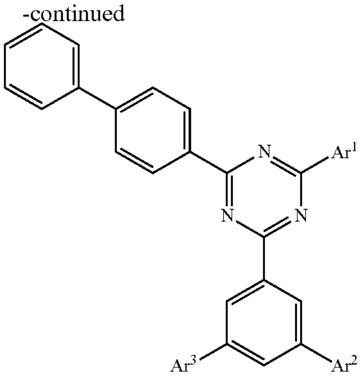

(1)

In the reaction formulas (a) to (f), $Ar^1$, $Ar^2$ and $Ar^3$ are as defined in the formula (1).

$X^2$ and $X^3$ each independently represent a leaving group. The leaving group is not particularly limited, and examples thereof include a chlorine atom, a bromine atom, an iodine atom, a trifluoromethanesulfonyloxy group, and the like. Among these, a bromine atom or a chlorine atom is preferable in light of favorable reaction yields. Nonetheless, in some cases, the use of the trifluoromethanesulfonyloxy group is more preferable due to the availability of a raw material.

$Y^2$ and $Y^3$ each independently represent a metal-containing group $ZnR^1$, $MgR^2$, or $Sn(R^3)_3$; or a boron-containing group $B(OR^4)_2$, wherein $R^1$ and $R^2$ each independently represent a chlorine atom, a bromine atom or an iodine atom; $R^3$ represents an alkyl group having 1 to 4 carbon atoms or a phenyl group; $R^4$ represents a hydrogen atom, an alkyl group having 1 to 4 carbon atoms or a phenyl group, wherein two $R^4$ of $B(OR^4)_2$ may be identical to or different from each other, and the two $R^4$ may taken together form a ring including the oxygen atom and the boron atom.

Examples of $ZnR^1$ and $MgR^2$ include ZnCl, ZnBr, ZnI, MgCl, MgBr, MgI, and the like. Examples of $Sn(R^3)_3$ include $Sn(Me)_3$, $Sn(Bu)_3$, and the like. Examples of $B(OR^4)_2$ include $B(OH)_2$, $B(OMe)_2$, $B(O^{i}Pr)_2$, $B(OBu)_2$, and the like. In addition, examples of $B(OR^4)_2$ in the case where two $R^4$ taken together form a ring including the oxygen atom and the boron atom include, but are not particularly limited to, groups represented by the following formulas (I) to (VI), and the group represented by the formula (II) is desirable in light of favorable yields.

[Chem. 18]

(I)

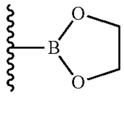

(II)

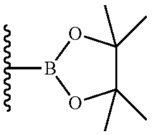

-continued (III)

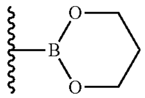

(IV)

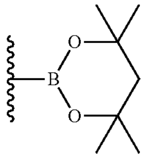

(V)

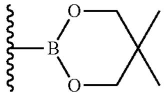

(VI)

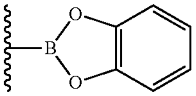

The production methods shown by the reaction formulas (a) to (d) will be described in more detail using, as an example, the production method shown by the reaction formula (a). The production method shown by the reaction formula (a) illustrates that $Y^2$—$Ar^2$ and $Y^3$—$Ar^3$ are used sequentially in the reactions in the presence of a palladium catalyst to obtain the cyclic azine compound (1). For $Y^2$—$Ar^2$ and $Y^3$—$Ar^3$ used in the reaction, $Y^2$—$Ar^2$ and $Y^3$—$Ar^3$ may be simultaneously used together for the reaction; alternatively, an intermediate product obtained by the reaction with $Y^2$—$Ar^2$ may be once isolated, and subsequently, the reaction of the intermediate product with $Y^3$—$Ar^3$ may be conducted in the presence of the palladium catalyst to obtain the cyclic azine compound (1). Further, $Y^3$—$Ar^3$ may be first subjected to the reaction to obtain the cyclic azine compound (1).

The production methods represented by the reaction formulas (e) and (f) will be described in more detail using, as an example, the production method shown by the reaction formula (e). The production method shown by the reaction formula (e) illustrates that $X^3$—$Ar^3$ is used in the reaction in the presence of a palladium catalyst to obtain the cyclic azine compound (1). In addition, the raw material used in the production methods shown by the reaction formulas (e) and (f), i.e., a cyclic azine compound, can be produced according to, for example, PCT International Publication No. 2017/025164. Alternatively, a commercially available product may be used.

Among the production methods shown by these reaction formulas (a) to (f), the production method shown by the reaction formula (e) or (f) is preferable in light of the high purity of the resultant cyclic azine compound (1).

[Production Method of Cyclic Azine Compound]

A production method according to an aspect of the present disclosure is a method for producing a cyclic azine compound represented by formula (1), the method including: reacting a compound represented by formula (4) with a compound represented by formula (5), Scheme (g)

[Chem. 19]

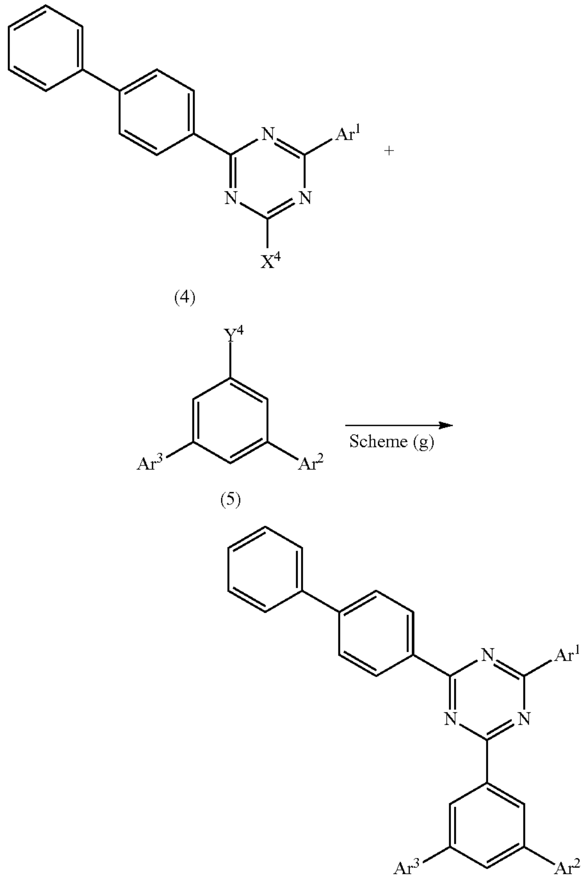

(4) (5) (1)

wherein in the formulas, $Ar^1$ represents a phenyl group or a 4-biphenylyl group;

$Ar^2$ represents a group represented by any one of formulas (2-1) to (2-3):

[Chem. 20]

(2-1)

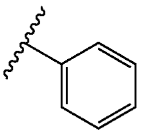

(2-2)

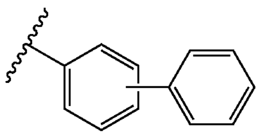

-continued (2-3)

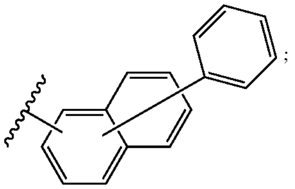

and $Ar^3$ represents a group represented by formula (3);

[Chem. 21]

(3)

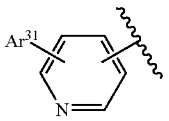

wherein $Ar^{31}$ represents:

a hydrogen atom, or a group represented by any one of the formulas (2-1) to (2-3);

$X^4$ represents a leaving group; and $Y^4$ represents a halogen atom, a metal-containing group, or a boron-containing group.

In this regard, the definition of the leaving group in the formula (4) is the same as the definition of the leaving group in the reaction formulas (a) to (f) described above. In addition, the definition of the metal-containing group or the boron-containing group in the formula (5) is the same as the definition of the leaving group in the reaction formulas (a) to (f) described above.

According to the aspect described above, a production method of a cyclic azine compound capable of producing a cyclic azine compound exhibiting both excellent driving voltage characteristics and excellent current efficiency characteristics can be provided.

[Pyridine Compound]

A pyridine compound according to an aspect of the present disclosure is represented by formula (5):

[Chem. 22]

(5)

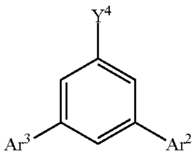

wherein in the formula, $Ar^2$ represents a group represented by any one of formulas (2-1) to (2-3):

[Chem. 23]

(2-1)

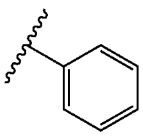

-continued (2-2)

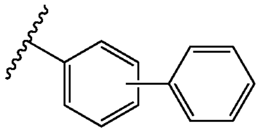

(2-3)

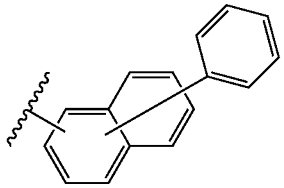

;

and $Ar^3$ represents a group represented by formula (3);

[Chem. 24]

(3)

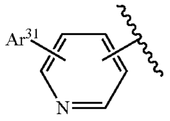

wherein $Ar^{31}$ represents:

a hydrogen atom, or a group represented by any one of the formulas (2-1) to (2-3); and $Y^4$ represents a halogen atom, a metal-containing group, or a boron-containing group.

In this regard, the definition of the metal-containing group or the boron-containing group in the formula (5) is the same as the definition of the leaving group in the reaction formulas (a) to (f) described above.

The pyridine compound represented by formula (5) is preferably a pyridine compound represented by formula (5-1), (5-2) or (5-3):

[Chem. 25]

(5-1)

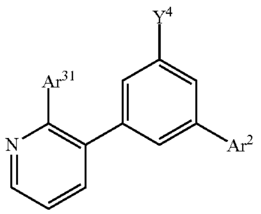

-continued (5-2)

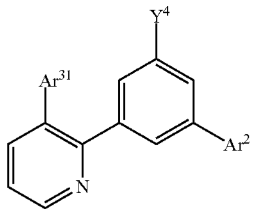

(5-3)

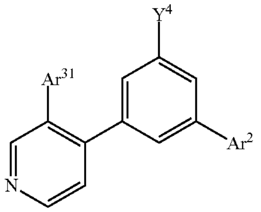

wherein in the formulas, $Ar^2$ and $Y^4$ are as defined in the formula (5); and $Ar^{31}$ is as defined in the formula (3).

According to the aspect described above, a pyridine compound that contributes to the production of a cyclic azine compound exhibiting both excellent driving voltage characteristics and excellent current efficiency characteristics can be provided.

EXAMPLES

Hereinafter, the present disclosure is described in further detail by way of Examples, but the present disclosure should in no way be construed to be limited to these Examples.

Measurements of $^1H$-NMR spectra were conducted on Gemini 200 (manufactured by Varian) or Bruker ASCEND 400 (400 MHz; manufactured by BRUKER). The light emission characteristics of the organic light emitting diodes were evaluated by applying direct current to the fabricated elements at room temperature, and by using a luminance meter (product name: BM-9, manufactured by Topcon Technohouse Corporation).

Synthesis Example—1

[Chem. 26]

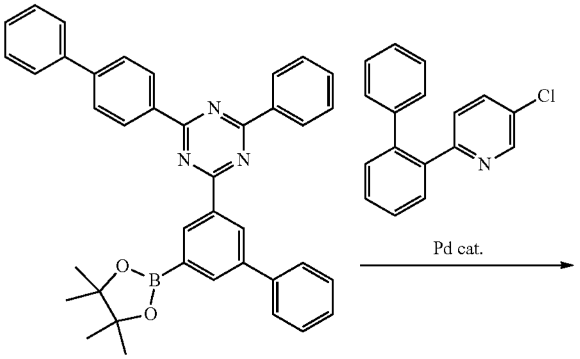

-continued

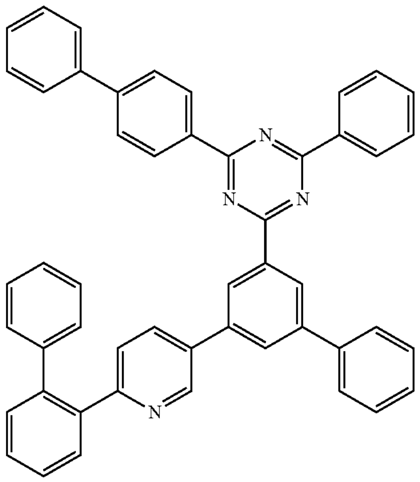

(1-6)

Under argon atmosphere, 2-(4-biphenylyl)-4-phenyl-6-[5-(4,4,5,5-tetramethyl-1,3,2-dioxaborolan-2-yl)-biphenyl-3-yl]-1,3,5-triazine (2.60 g, 4.4 mmol), 6-(2-biphenylyl)-3-chloropyridine (1.25 g, 4.9 mmol), a 2 M aqueous potassium phosphate solution (6.6 mL), palladium acetate (30 mg, 0.13 mmol) and 2-dicyclohexylphosphino-2',6'-diisopropoxybiphenyl (RuPhos, 124 mg, 0.27 mmol) were suspended in diethylene glycol dimethyl ether (diglyme, 40 mL), and stirred at 150° C. for 27 h. After cooling, water was added to the reaction mixture, and the solid was filtered, and washed with water and methanol. The obtained solid was dissolved in hot toluene, activated charcoal was added thereto, and the mixture was filtered through Celite. After the obtained solution was cooled to room temperature, the precipitated white solid was collected to obtain 2-(4-biphenylyl)-4-phenyl-6-{5-[6-(2-biphenylyl)-pyridyl-3-yl]-biphenyl-3-yl}-1,3,5-triazine (1-6) (amount 2.62 g, yield 85%).

$^{1}$H-NMR (400 MHz, $CDCl_3$): δ 9.14 (dd, J=2.3, 0.7 Hz, 1H), 9.01 (dd, J=1.8, 1.5 Hz, 2H), 8.86 (d, J=8.9 Hz, 2H), 8.81 (d, J=6.5 Hz, 2H), 8.02 (dd, J=1.8, 1.5 Hz, 1H), 7.84-7.86 (m, 2H), 7.83 (d, J=8.6 Hz, 2H), 7.80 (d, J=8.4 Hz, 2H), 7.72 (d, J=7.1 Hz, 2H), 7.46-7.65 (m, 11H), 7.43 (t, J=7.3 Hz, 1H), 7.28-7.33 (m, 4H), 7.08-7.14 (m, 1H), 7.06 (d, J=8.1 Hz, 1H).

Synthesis Example—2

[Chem. 27]

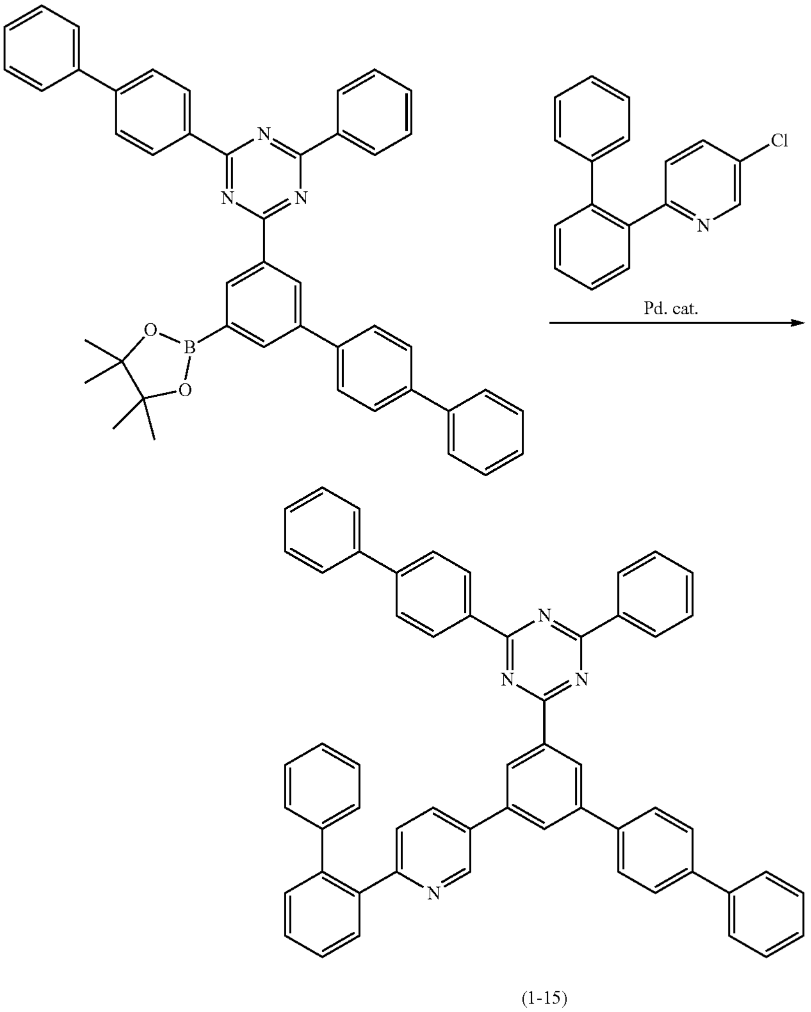

(1-15)

Under argon atmosphere, a 2 M aqueous potassium phosphate solution (3.8 mL) was added to a solution of 2-(4-biphenylyl)-4-phenyl-6-[5-(4,4,5,5-tetramethyl-1,3,2-dioxaborolan-2-yl)-1,1': 4',1"-terphenyl-3-yl]-1,3,5-triazine, 2-(2-biphenyl)-5-chloropyridine (731 mg, 2.8 mmol), palladium acetate (17 mg, 0.075 mmol), and RuPhos (70 mg, 0.15 mmol) in diglyme (25 mL), and the mixture was stirred at 150° C. for 3 h. After cooling to room temperature, water and methanol were added to the reaction solution, and the solid was filtered, and washed with water and then methanol. After drying under reduced pressure, the obtained solid was dissolved in toluene (450 mL) under reflux, activated carbon (0.4 g) was added, then then the activated carbon was filtered off from the suspension, and washed with hot toluene (150 mL). Toluene was evaporated from the filtrate, and the obtained solid was dried to dryness under reduced pressure, followed by purification by recrystallization (xylene) to obtain 2-(4-biphenylyl)-4-{5-[6-(2-biphenylyl)pyridyl-3-yl]-1,1':4',1"-terphenyl-3-yl}-6-phenyl-1,3,5-triazine (1-15) as a white solid (1.66 g, 96%).

$^1$H-NMR ($CDCl_3$): δ 9.14 (d, J=1.7 Hz, 1H), 9.05 (dd, J=1.5, 1.5 Hz, 1H), 9.00 (dd, J=1.5, 1.5 Hz, 1H), 8.86 (d, J=8.4 Hz, 2H), 8.81 (dd, J=8.2, 1.7 Hz, 2H), 8.06 (dd, J=1.5, 1.5 Hz, 1H), 7.88 (d, J=8.4 Hz, 2H), 7.79-7.83 (m, 2H), 7.82 (d, J=8.2 Hz, 2H), 7.79 (d, J=8.2 Hz, 2H), 7.72 (d, J=7.3 Hz, 2H), 7.70 (d, J=7.3 Hz, 2H), 7.59-7.63 (m, 3H), 7.42-7.59 (m, 7H), 7.42 (dd, J=7.3, 7.3 Hz, 1H), 7.40 (dd, J=7.3, 7.3 Hz, 1H), 7.26-7.38 (m, 5H), 7.06 (d, J 8.2 Hz, 1H).

Synthesis Example—5

[Chem. 28]

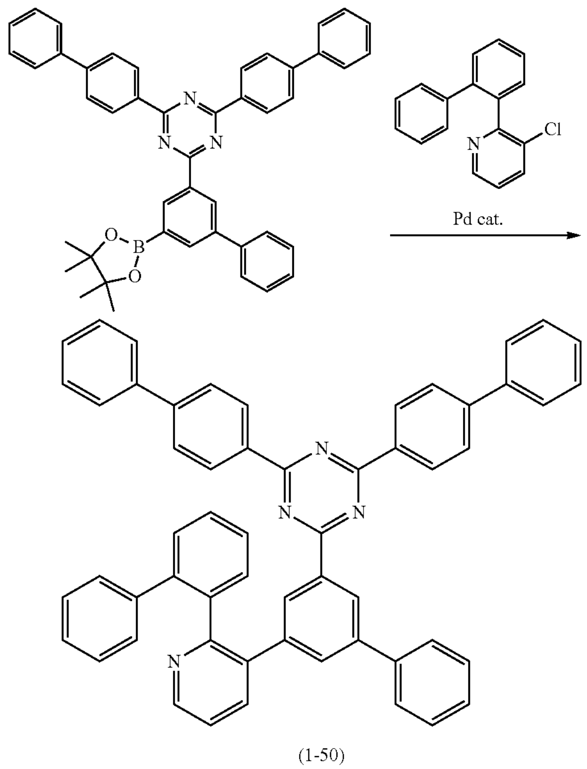

(1-50)

Under argon atmosphere, 2,4-bis(4-biphenylyl)-6-[5-(4,4,5,5-tetramethyl-1,3,2-dioxaborolan-2-yl)-biphenyl-3-yl]-1,3,5-triazine (1.99 g, 3.0 mmol), 2-(2-biphenylyl)-3-chloropyridine (0.88 g, 3.3 mmol), palladium acetate (20 mg, 0.09 mmol) and a toluene solution of tricyclohexylphosphine (0.6 M, 0.3 mL, 0.18 mmol) were suspended in N,N-dimethylformamide (DMF, 30 mL). A 2 M aqueous potassium phosphate solution (4.5 mL) was added to this suspension, and the mixture was heated under reflux for 22 h. After cooling, water and methanol were added to the reaction mixture, and the precipitated solid was filtered. The obtained solid was purified by recrystallization (toluene) to obtain the desired 2,4-bis(4-biphenylyl)-6-{5-[2-(2-biphenylyl)pyridin-3-yl]-biphenyl-3-yl}-1,3,5-triazine (1-50) (1.74 g, 2.3 mmol, 76%). $^1$H-NMR ($CDCl_3$): δ8.78-8.82 (m, 6H), 7.91 (s, 1H), 7.90 (dd, J=8.8, 0.9 Hz, 1H), 7.83 (d, J=8.8 Hz, 4H), 7.71-7.75 (m, 4H), 7.52 (dd, J=7.6 Hz, 4H), 7.37-7.48 (m, 9H), 7.15 (dd, J=7.6, 0.9 Hz, 4H), 6.99 (t, J=3.5 Hz, 1H), 6.94 (dt, J=7.3, 1.3 Hz, 1H), 6.87 (t, J=7.4 Hz, 1H), 6.55 (dd, J=8.3, 1.6 Hz, 2H).

Synthesis Example—6

[Chem. 29]

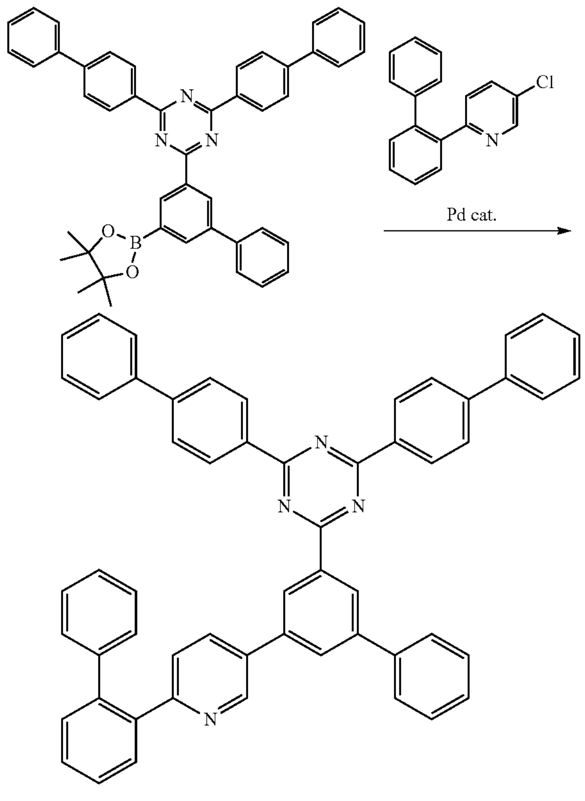

(1-51)

Under argon atmosphere, a 2 M aqueous potassium phosphate solution (13.5 mL) was added to a solution of 2,4-bis(4-biphenylyl)-6-{5-(4,4,5,5-tetramethyl-1,3,2-dioxaborolan-2-yl)biphenyl-3-yl}-1,3,5-triazine (5.97 g, 9.0 mmol), 2-(2-biphenylyl)-5-chloropyridine (2.63 g, 9.9 mmol), palladium acetate (61 mg, 0.27 mmol), and RuPhos (252 mg, 0.54 mmol) in diglyme (90 mL), and the mixture was stirred at 150° C. for 3 h. After cooling to room temperature, water and methanol were added to the reaction solution, and the solid was filtered, and washed with water and then methanol.

After drying under reduced pressure, the obtained solid was dissolved in toluene (500 mL) under reflux, activated carbon (2.0 g) was added, then the activated carbon was filtered off from the suspension, and washed with toluene (200 mL). Low-boiling point components were evaporated from the filtrate under reduced pressure, followed by purification by recrystallization (xylene) to obtain 2,4-bis(4-biphenylyl)-6-{5-[6-(2-biphenyl)pyridin-3-yl]biphenyl-3-yl}-1,3,5-triazine (1-51) as a white solid (4.76 g, 69%).

$^1$H-NMR ($CDCl_3$): δ 9.13 (d, J=1.8 Hz, 1H), 9.02 (dd, J=1.6, 1.6 Hz, 1H), 9.00 (dd, J=1.6, 1.6 Hz, 1H), 8.86 (d, J=8.4 Hz, 4H), 8.01 (dd, J=1.6, 1.6 Hz, 1H), 7.88-7.80 (m, 2H), 7.82 (d, J=8.4 Hz, 4H), 7.80 (d, J=7.2 Hz, 2H), 7.72 (d, J=7.2 Hz, 4H), 7.56 (dd, J=7.3, 7.3 Hz, 2H), 7.47-7.54 (m, 3H), 7.51 (dd, J=7.3, 7.3 Hz, 4H), 7.47 (d, J=7.5 Hz, 1H), 7.42 (dd, J=7.3, 7.3 Hz, 2H), 7.26-7.36 (m, 5H), 7.05 (d, J=8.1 Hz, 1H).

Synthesis Example—9

[Chem. 30]

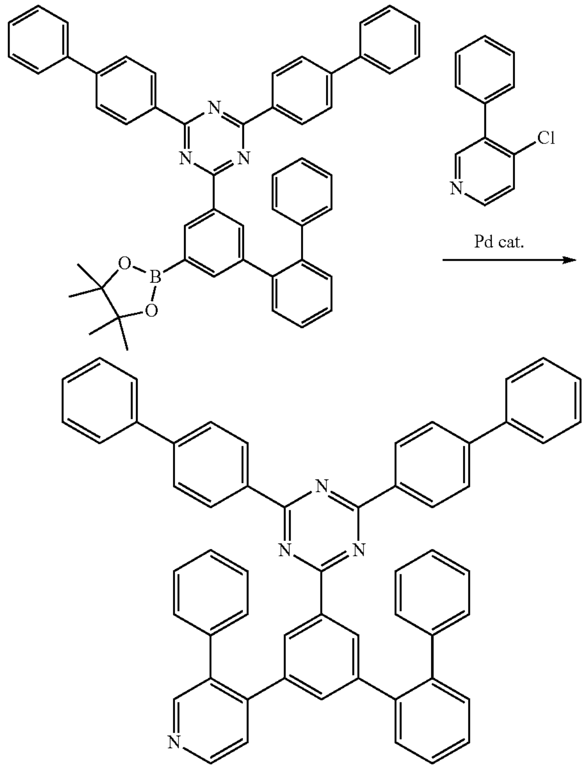

(1-65)

Under argon atmosphere, 2,4-bis(4-biphenylyl)-6-{5-(4,4,5,5-tetramethyl-1,3,2-dioxaborolan-2-yl)-1,1':2',1"-terphenyl-3-yl}-1,3,5-triazine (2.22 g, 3.0 mmol), 4-chloro-3-phenylpyridine (853 mg, 4.5 mmol), and palladium acetate (14 mg, 0.06 mmol) were suspended in DMF (30 mL). A toluene solution of tricyclohexylphosphine (0.6 M, 0.2 mL, 0.12 mmol), and 2 M potassium phosphate (4.5 mL) were added to this suspension, and the mixture was stirred overnight at 130° C. After cooling to room temperature, water and methanol was added, and the precipitated solid was filtered. The solid was washed with water and then methanol, and thereafter low-boiling point components were evaporated under reduced pressure. The obtained solid was purified by column chromatography (hexane:chloroform=3:1), and then recrystallization from toluene to obtain the desired 2,4-bis(4-biphenylyl)-6-{5-(3-phenylpyridin-4-yl)-1,1':2',1"-terphenyl-3-yl)}-1,3,5-triazine (1-65) (1.49 g, 64%). $^1$H-NMR ($CDCl_3$): δ 8.69-8.71 (m, 5H), 8.62 (d, J=5.0 Hz, 1H), 8.52 (t, J=1.6 Hz, 1H), 8.36 (t, J=1.6 Hz, 1H), 7.80 (d, J=8.5 Hz, 4H), 7.72 (dd, J=7.1, 1.4 Hz, 4H), 7.41-7.54 (m, 9H), 7.21-7.39 (m, 12H), 7.12 (d, J=4.6 Hz, 1H).

Synthesis Example—10

[Chem. 31]

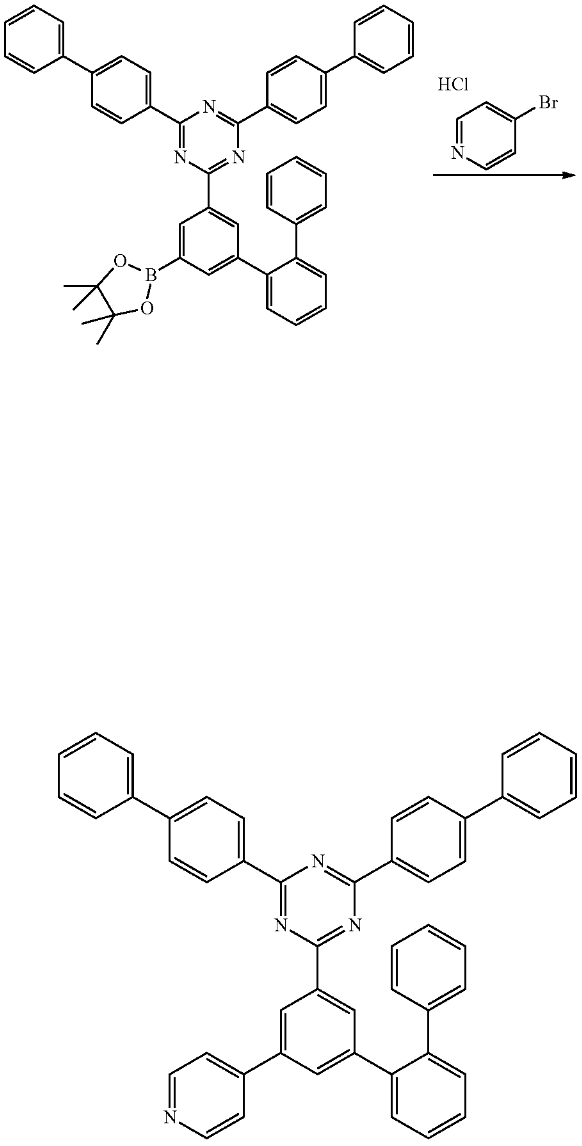

(1-64)

Under nitrogen atmosphere, 2,4-bis(4-biphenylyl)-6-{5-(4,4,5,5-tetramethyl-1,3,2-dioxaborolan-2-yl)-1,1':2',1"-terphenyl-3-yl}-1,3,5-triazine (85 g, 115 mmol), 4-bromopyridine hydrochloride (33.5 g, 172 mmol) and tetrakis (triphenylphosphine)palladium (5.3 g, 4.6 mmol) were suspended in THE (1.15 L). A 2 M aqueous potassium phosphate solution (345 mL) was added to this suspension, and the mixture was heated under reflux for 5 h. After cooling, water and methanol were added, and the precipitates were filtered. The filtered product was purified by recrystallization from toluene to obtain the desired 2,4-bis (4-biphenylyl)-6-{5-(4-pyridyl)-1,1':2',1"-terphenyl-3-yl}-1,3,5-triazine (1-64) (59.8 g, 75%).

Synthesis Example—11

[Chem. 32]

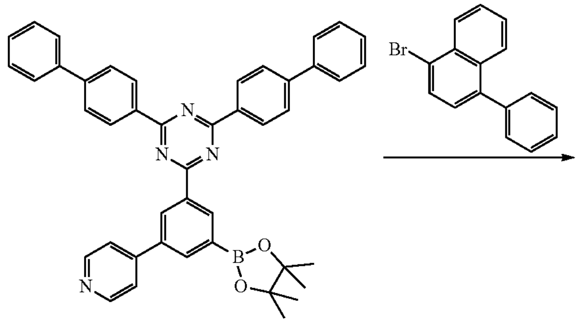

-continued

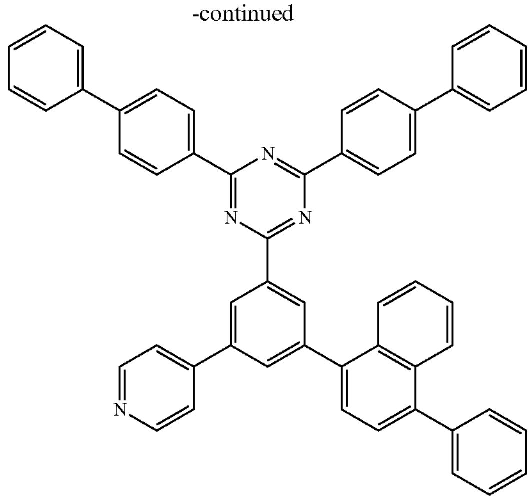

(1-73)

Under argon atmosphere, 2,4-bis(4-biphenylyl)-6-(3-(4,4,5,5-tetramethyl-1,3,2-dioxaborolan-2-yl)-5-(4-pyridyl)phenyl)-1,3,5-triazine (3.00 g, 4.5 mmol), 1-bromo-4-phenylnaphthalene (1.66 g, 5.9 mmol), and tetrakis (triphenylphosphine)palladium (156 mg, 0.13 mmol) were suspended in THE (45 mL). A 2 M aqueous potassium carbonate solution (6.7 mL) was added to this suspension, and the mixture was heated under reflux for 22 h. After cooling, water and methanol were added to the reaction mixture, and the precipitated solid was filtered. The obtained solid was purified by recrystallization (toluene) to obtain the desired 2,4-bis(4-biphenylyl)-6-[3-(4-phenyl-naphthalen-1-yl)-5-(4-pyridyl)phenyl]-1,3,5-triazine (1-73) (2.67 g, 80%).

$^1$H-NMR ($CDCl_3$) δ 9.17 (t, J=1.6 Hz, 1H), 9.05 (t, J=1.6 Hz, 1H), 8.87 (dt, J=8.6, 1.8 Hz, 4H), 8.78 (dd, J=4.6, 1.6 Hz, 2H), 8.04-8.07 (m, 3H), 7.82 (dt, J=8.6, 1.6 Hz, 4H), 7.77 (dd, J=4.6, 1.6 Hz, 2H), 7.71 (dt, J=7.0, 2.0 Hz, 4H), 7.68 (d, J=7.2 Hz, 1H), 7.47-7.62 (m, 12H), 7.42 (tt, J=7.3, 2.1 Hz, 2H).

Synthesis Example—12

[Chem. 33]

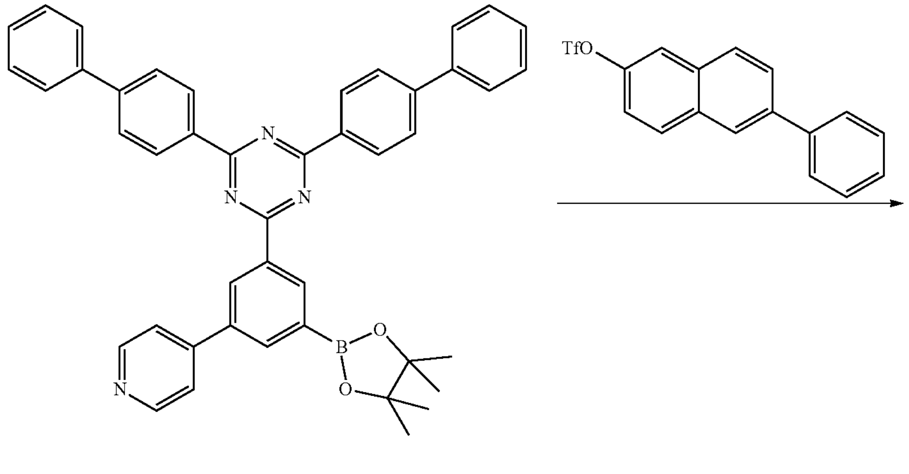

-continued

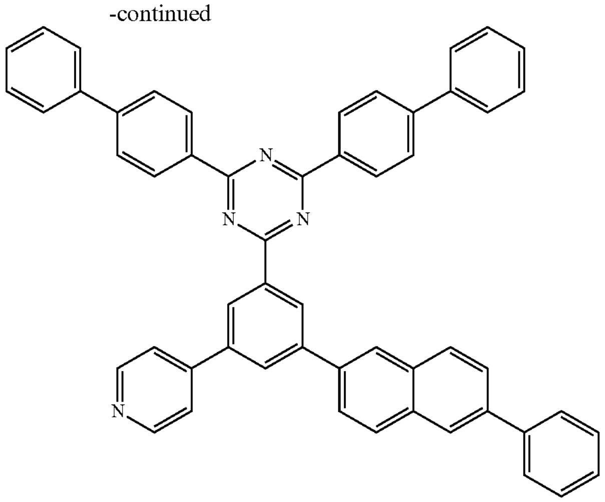

Under argon atmosphere, 2,4-bis(4-biphenylyl)-6-[3-(4,4,5,5-tetramethyl-1,3,2-dioxaborolan-2-yl)-5-(4-pyridyl)phenyl]-1,3,5-triazine (3.50 g, 5.3 mmol), 6-phenyl-2-trifluoromethanesulfonyloxynaphthalene (2.41 g, 6.8 mmol), palladium acetate (60 mg, 0.27 mmol) and 2-dicyclohexylphosphino-2',4',6'-triisopropylbiphenyl (XPhos, 252 mg, 0.53 mmol) were suspended in THF (55 mL). A 2 M aqueous potassium carbonate solution (7.7 mL) was added to this suspension, and the mixture was heated under reflux for 15 h. After cooling to room temperature, water and methanol were added to the reaction mixture, and the precipitated solid was filtered. The obtained solid was purified by recrystallization (toluene) to obtain the desired 2,4-bis(4-biphenylyl)-6-[3-(6-phenyl-naphthalen-2-yl)-5-(4-pyridyl)phenyl]-1,3,5-triazine (1-92) (3.21 g, 4.3 mmol, 8.3). $^1$H-NMR ($CDCl_3$): δ 9.22 (t, 1.5 Hz, 1H), 9.06 (t, 1.5 Hz, 1H), 6.91 (d, J=8.4 Hz, 4H), 8.81 (dd, J=3.1, 1.5 Hz, 2H), 8.29 (s, 1H), 3.23 (t, J=1.5 Hz, 1H), 8.15 (s, 1H), 8.10 (t, J=8.3 Hz, 2H), 7.98 (dt, J=8.9, 1.7 Hz, 1H), 7.86 (dt, J=8.3, 1.9 Hz, 4H), 7.78 (t, J=6.3 Hz, 4H), 7.73 (dd, J=8.4, 1.4 Hz, 4H), 7.56-7.50 (m, 7H), 7.46-7.41 (m, 3H).

Synthesis Example—13

[Chem. 34]

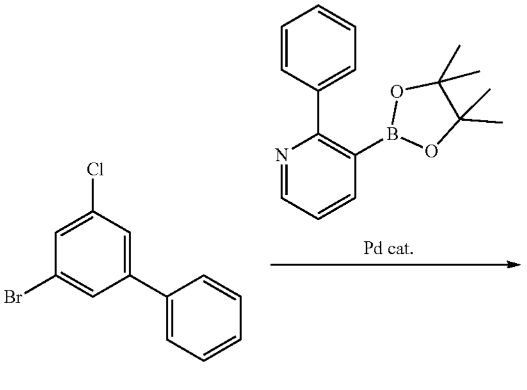

-continued

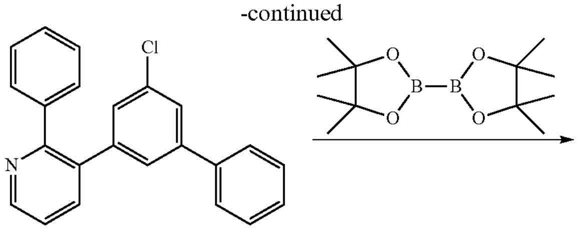

(5-1)

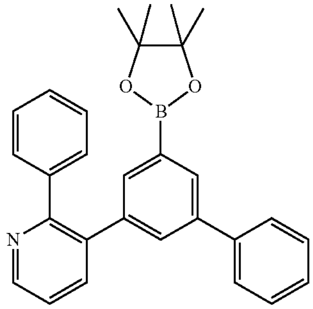

(5-2)

Under nitrogen atmosphere, 3-bromo-5-chlorobiphenyl (50 g, 186.9 mmol), 3-(4,4,5,5-tetramethyl-1,3,2-dioxaborolan-2-yl)-2-phenylpyridine (63 g, 224.3 mmol), and tetrakis (triphenylphosphine)palladium (4.3 g, 3.7 mmol) were suspended in THF (370 mL) at 60° C. A 4 M potassium phosphate (140 mL) was added to this suspension, and the mixture was heated under reflux for 10 h. After cooling to room temperature, toluene was added to the reaction mixture, and the organic layer was extracted. Magnesium sulfate and activated charcoal were added to the organic layer, and insoluble components were filtered off. The filtrate was concentrated, and then purified by recrystallization from ethanol to obtain the desired 3-chloro-5-(2-phenylpyridin-3-yl)biphenyl (5-1) (45.5 g, 71%).

$^1$H-NMR ($CDCl_3$): δ 8.73 (dd, 4.8, 1.7 Hz, 1H), 7.79 (dd, t. t, 1.7 Hz, 1H), 7.46 (t, 1.8 Hz, 1H), 7.42-7.30 (m, 9H), 7.27 (d, 1.8 Hz, 1H), 7.25-7.24 (m, 2H), 7.18 (t, 1.6 Hz, 1H).

Under nitrogen atmosphere, the compound 5-1 (197.8 g, 578.7 mmol), bis(pinacolato)diboron (154.3 g, 607.7 mmol) and potassium acetate (170.4 g, 1736 mmol) were suspended in THF (1.16 L) at 60° C. A THF solution (30 mL) of palladium acetate (1.3 g, 5.8 mmol) and 2-dicyclohexylphosphino-2',4',6'-triisopropylbiphenyl (XPhos, 5.5 mg, 11.6 mmol) were added to this suspension, and the mixture was heated under reflux for 6 h. After cooling to room temperature, activated charcoal was added to the reaction mixture followed by stirring, and then insoluble components were filtered off. The filtrate was concentrated, and then purified by recrystallization from hexane to obtain the desired 3-(4,4,5,5-tetramethyl-1,3,2-dioxaborolan-2-yl)-5-(2-phenylpyridin-3-yl) biphenyl (5-2) (178 g, 71%).

$^1$H-NMR ($CDCl_3$): δ 8.70 (dd, 4.8, 1.7 Hz, 1H), 7.92 (dd, 1.8, 1.0 Hz, 1H), 7.86 (dd, 7.7, 1.7 Hz, 1H), 7.79 (dd, 1.8, 1.0 Hz, 1H), 7.41-7.38 (m, 2H), 7.36-7.27 (m, 8H), 7.23-7.21 (m, 2H), 1.36 (s, 12H).

Synthesis Example—14

Under nitrogen atmosphere, 2-chloro-4,6-di(4-biphenylyl)triazine (176.2 g, 420 mmol), the compound 5-2 (200 g, 462 mmol), and tetrakis(triphenylphosphine)palladium (4.9 g, 4.2 mmol) were suspended in THF (4.2 L). A 2 M aqueous potassium phosphate solution (0.6 L) was added to this suspension, and the mixture was heated under reflux for 6 h. After cooling to room temperature, methanol was added, and the precipitates were filtered. The filtered product and activated charcoal were suspended in toluene at 80° C., and then insolubles were filtered off. The filtrate was concentrated, and then purified by recrystallization from toluene to obtain the desired 4,6-di(4-biphenylyl)-2-[5-(2-phenylpyridin-3-yl)biphenyl-3-yl]-1,3,5-triazine (1-48) (182 g, 63%).

$^1$H-NMR ($CDCl_3$): δ 9.02 (t, 1.6 Jz, 1H), 8.90 (d, 8.6 Hz, 4H), 8.80 (t, 1.6 Hz, 1H), 8.77 (dd, 4.7, 1.7 Hz, 1H), 8.09

[Chem. 35]

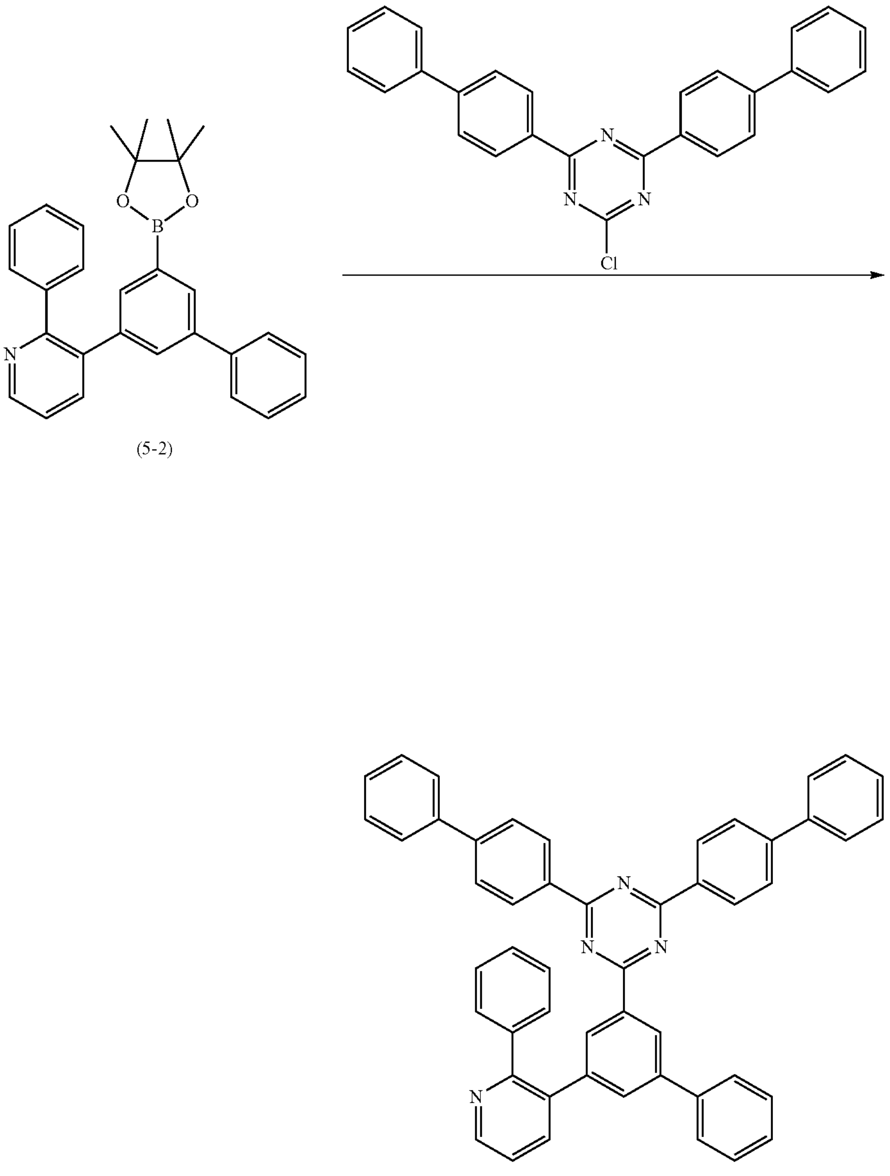

(5-2)

(1-48)

(dd, 7.7, 1.7 Hz, 1H), 7.93 (d, 8.6 Hz, 4H), 7.82 (d, 8.2 Hz, 4H), 7.77 (t, 1.8 Hz, 1H), 7.62-7.32 (m, 16H), 7.29 (tt, 7.3, 1.4 Hz, 1H).

Synthesis Example—15

[Chem. 36]

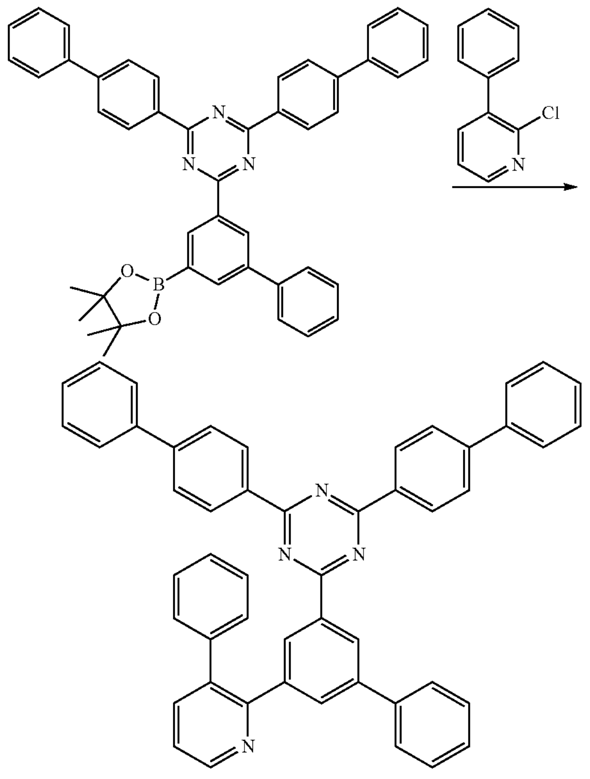

(1-54)

Under argon atmosphere, 4,6-bis(4-biphenylyl)-2-{3-(4,4,5,5-tetramethyl-1,3,2-dioxaborolan-2-yl) biphenylyl-5-yl}-1,3,5-triazine (3.0 g, 4.52 mmol), 2-chloro-3-phenylpyridine (943 mg, 4.97 mmol), palladium acetate (51 mg, 0.23 mmol), 2-dicyclohexylphosphino-2',6'-diisopropoxybiphenyl (202 mg, 0.45 mmol) were suspended in THF (46 mL). A 2.0 M aqueous potassium phosphate solution (7 mL) was added to this suspension, and the mixture was then heated under reflux for 24 h. After cooling, water and methanol were added to the reaction mixture. The resultant solid was filtered, and washed with hexane to obtain the desired 4,6-bis(4-biphenylyl)-2-{5-(3-phenyl-pyridyl-2-yl) biphenylyl-3-yl}-1,3,5-triazine (1-54) (2.92 g, 4.23 mmol, 94%).

$^1$H-NMR ($CDCl_3$) δ 7.36-7.55 (m, 17H), 7.01-7.75 (m, 4H), 7.80-7.88 (m, 6H), 8.79-8.84 (m, 5H), 8.87 (dd, J=1.6, 1.5 Hz, 1H), 8.93 (dd, J=1.7, 1.6 Hz, 1H).

Further, cyclic azine compounds represented by formulas (1-49), (1-52), (1-66), (1-67) and (1-71) were synthesized according to the procedures similar to the production methods described in Synthesis Examples—1 to 15.

The structural formulas and abbreviations of compounds used in the production of an organic light emitting diode containing the cyclic azine compound (1) as a constitutive component and in the performance evaluations are shown below.

[Chem. 37]

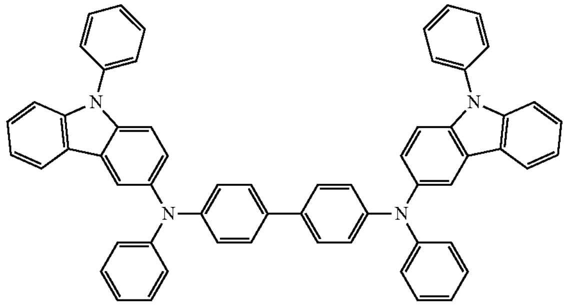

HIL

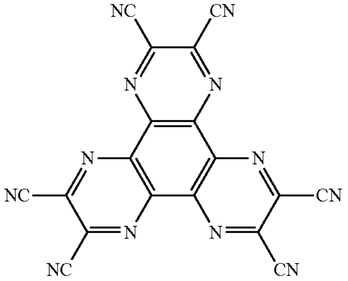

HAT-CN

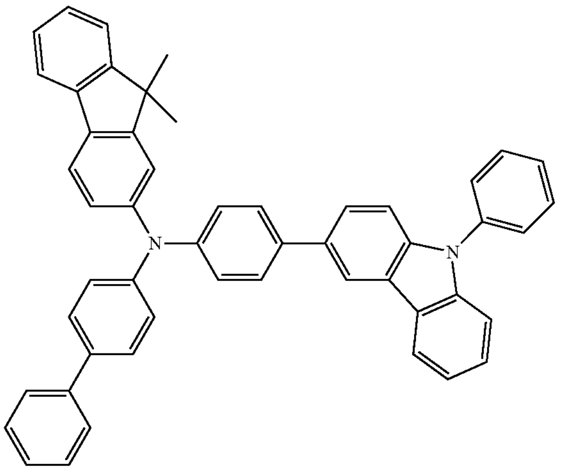

HTL

NDP-9

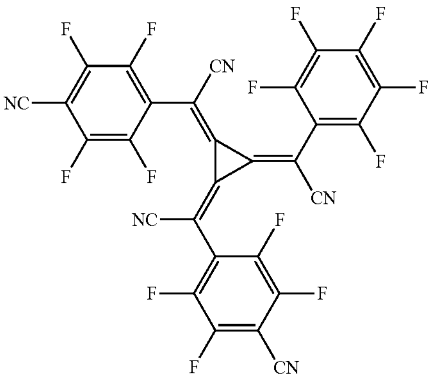

-continued
EBL-1
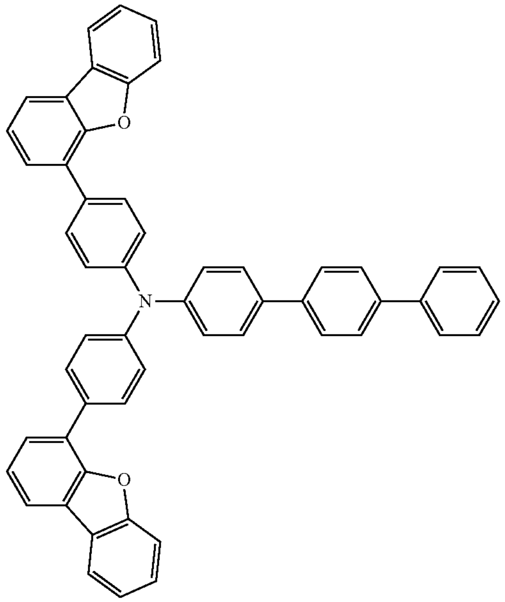
EBL-2
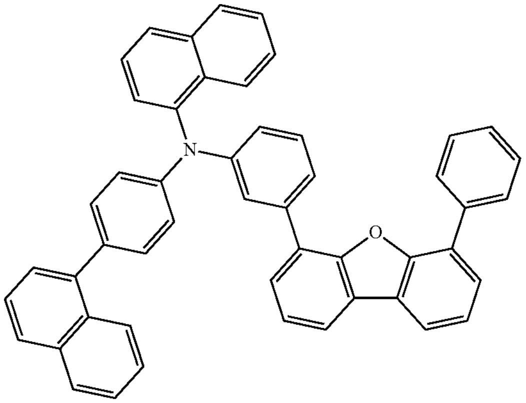
EBL-3
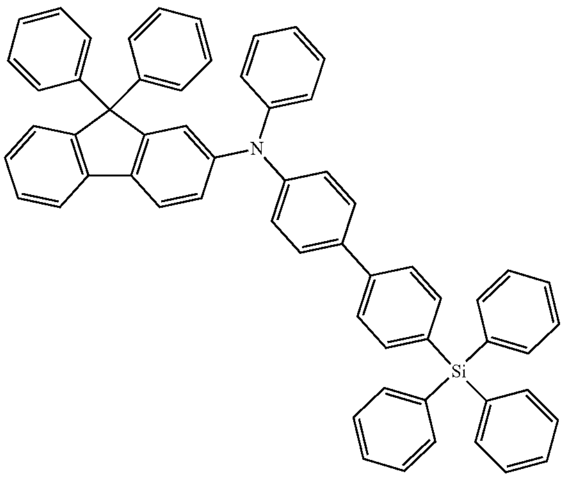
-continued
EBL-4
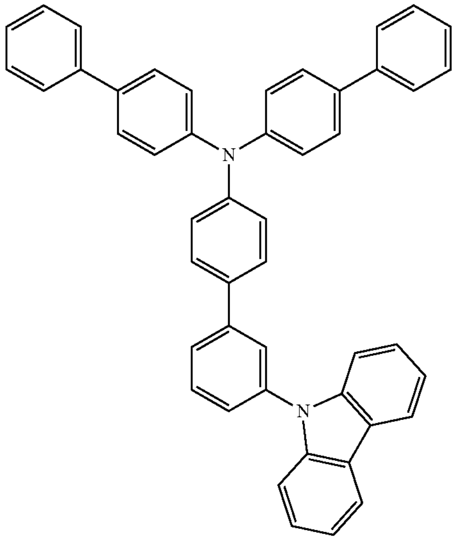
BH-1
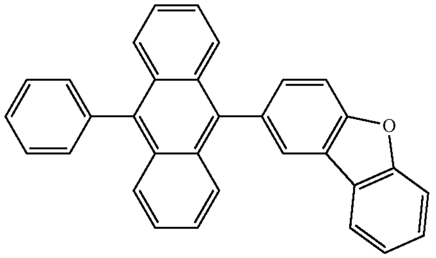
BH-2
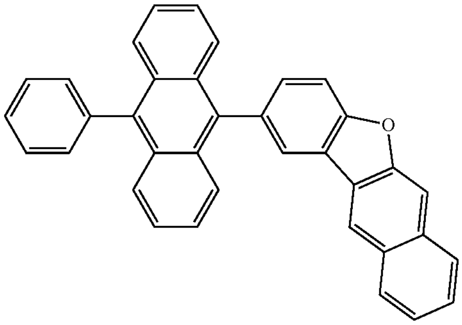
BD-1
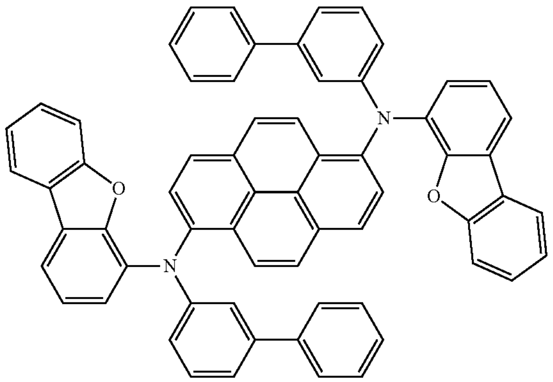

-continued
BD-2
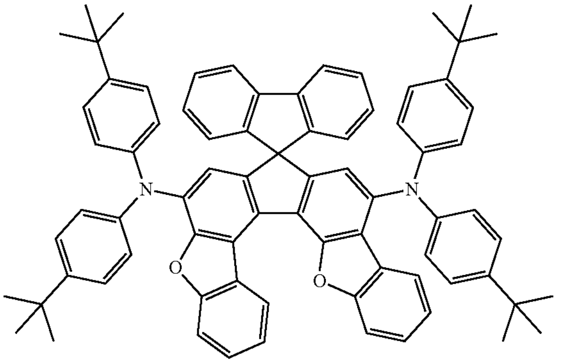
BD-3
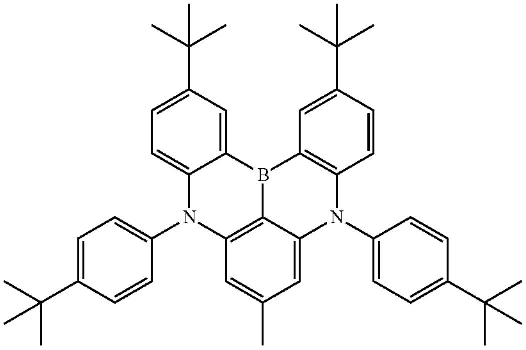
HBL-1
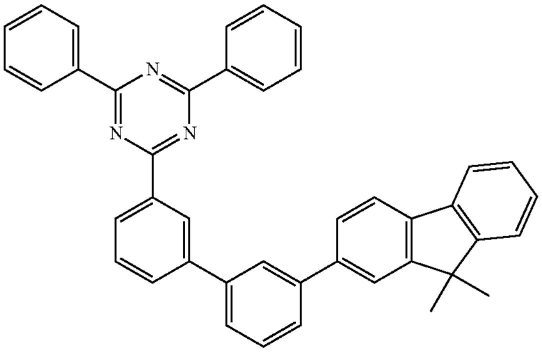
HBL-2
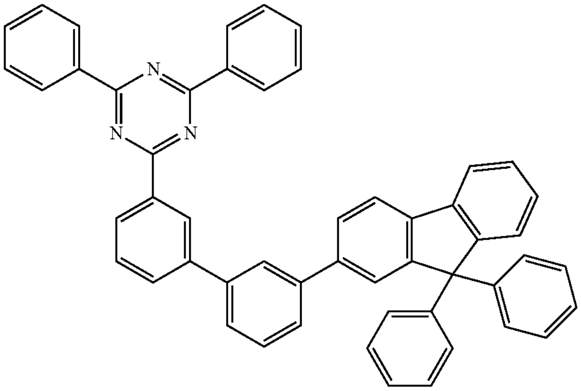
-continued
ETL-1
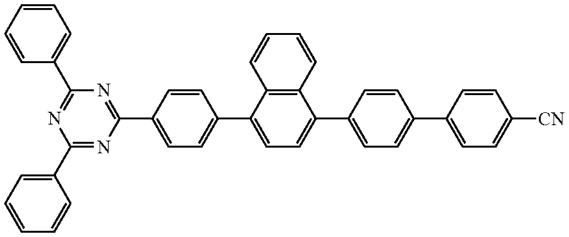
ETL-2
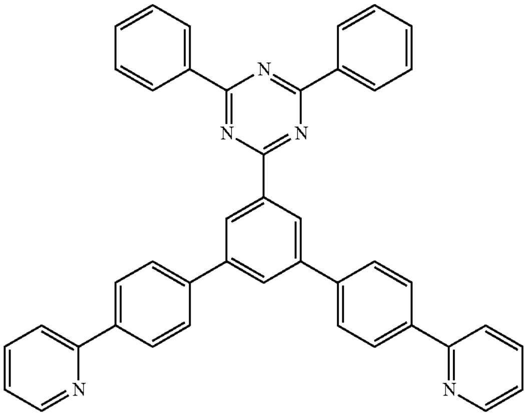
ETL-3
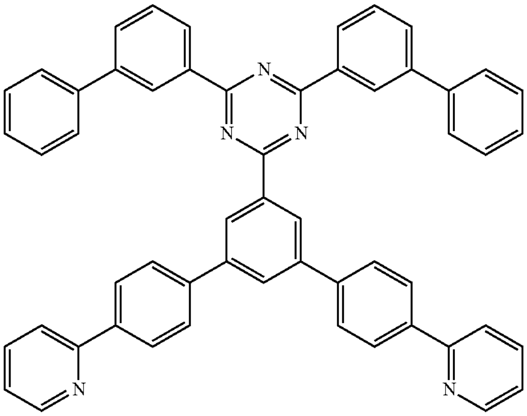
ETL-4
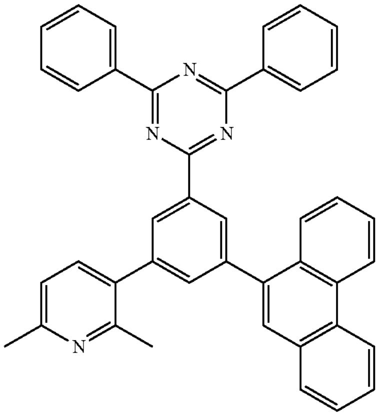

-continued

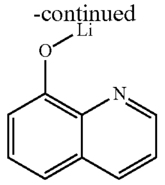

Liq

Figure 2:
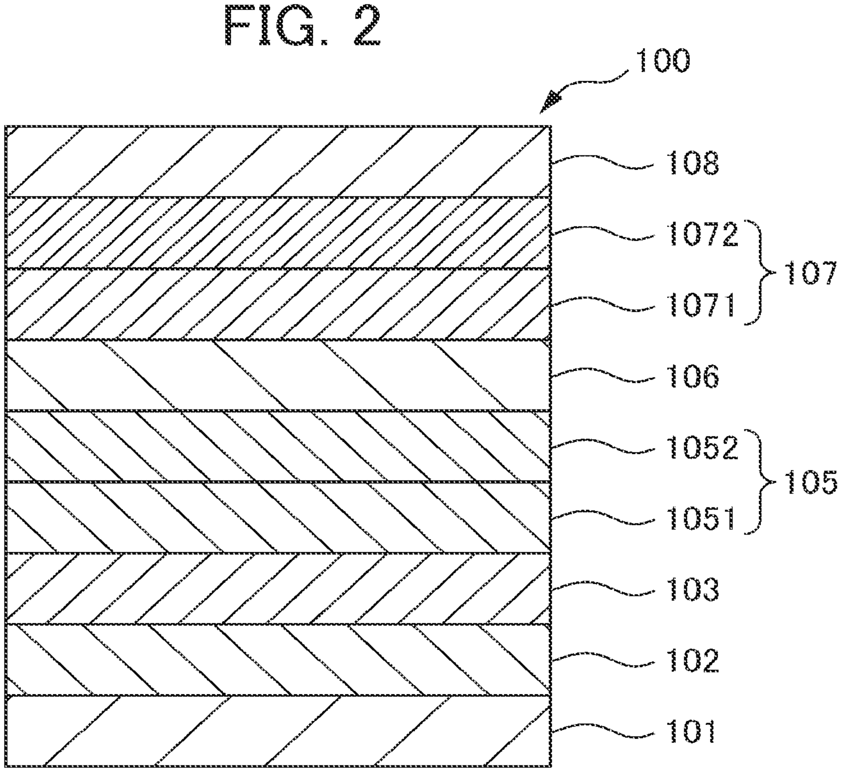
FIG. 2 is a schematic cross-sectional view showing an example (Element Example—1) of a layered structure of an organic light emitting diode containing a cyclic azine compound according to an aspect of the present disclosure.

Element Example—1 (See FIG. 2)

(Preparation of Substrate 101 and Anode 102)

As a substrate having an anode on the surface thereof, a glass substrate with an indium oxide-tin (ITO) transparent electrode formed of a 2 mm wide ITO film (thickness: 110 nm) and patterned in stripes was prepared. Then, this substrate was cleaned with isopropyl alcohol, and thereafter surface-treated by ozone ultraviolet ray cleaning.

(Preparation for Vacuum Deposition)

Each layer was vacuum deposited on the cleaned and surface-treated substrate by vacuum deposition procedure to form and laminate the layers. First, the glass substrate was introduced to a vacuum deposition chamber, and the pressure within the vacuum deposition chamber was reduced to $1.0\times10^{-4}$ Pa. Then, the layers were fabricated in the following order according to the respective film formation conditions.

(Fabrication of Hole Injection Layer 103)

A hole injection layer 103 was fabricated by depositing sublimation-purified HTL and NDP-9 at a rate of 0.15 nm/sec to achieve a film thickness of 10 nm.

(Fabrication of First Hole Transport Layer 1051)

A first hole transport layer 1051 was fabricated by depositing sublimation-purified HTL at a rate of 0.15 nm/sec to achieve a film thickness of 85 nm.

(Fabrication of Second Hole Transport Layer 1052)

A second hole transport layer 1052 was fabricated by depositing sublimation-purified EBL-3 at a rate of 0.15 nm/sec to achieve a film thickness of 5 nm.

(Fabrication of Light Emitting Layer 106)

A light emitting layer 106 was fabricated by depositing sublimation-purified BH-1 and BD-2 in a ratio of 95:5 (mass ratio) to achieve a film thickness of 20 nm. The film formation rate was 0.18 nm/sec.

(Fabrication of First Electron Transport Layer 1071)

A first electron transport layer 1071 was fabricated by depositing sublimation-purified HBL-1 at a rate of 0.05 nm/sec to achieve a film thickness of 6 nm.

(Fabrication of Second Electron Transport Layer 1072)

A second electron transport layer 1072 was fabricated by depositing the compound 1-48 and Liq in a ratio of 50:50 (mass ratio) to achieve a film thickness of 25 nm. The film formation rate was 0.15 nm/sec.

(Fabrication of Cathode 108)

Finally, a cathode 108 was formed using a metal mask placed so as to be perpendicular to the ITO stripes on the substrate. The cathode was formed by depositing silver/magnesium (mass ratio 1/10) and silver in this order to achieve a film thickness of 80 nm and 20 nm, respectively, and thus had a two-layer structure. The film formation rate for silver/magnesium was 0.5 nm/sec. and the film formation rate for silver was 0.2 nm/sec.

According to the procedure described above, an organic light emitting diode 100 having a light emission area of 4 $mm^2$, as shown in FIG. 2, was fabricated. It should be noted that the thickness of each layer was measured using a stylus profilometer (DEKTAK, manufactured by Bruker).

Furthermore, this element was encapsulated in a glove box under nitrogen atmosphere with an oxygen and moisture concentration of 1 ppm or less. The encapsulation was performed by encapsulating the deposition substrate (element) in a glass encapsulating cap using bisphenol F epoxy resin (manufactured by Nagase ChemteX Corporation).

Direct current was applied to the organic light emitting diode fabricated as described above, and light emission characteristics thereof was evaluated using a luminance meter (product name: BM-9, manufactured by Topcon Technohouse Corporation). Current efficiency (cd/A) under the application of a current density of 10 $mA/cm^2$ was measured as the light emission characteristics. It should be noted that the driving voltage shown below is a relative value with respect to the result of Element Reference Example 3 described below as a reference value (100). The obtained measurement results are shown in Table 4.

Element Comparative Example—1

An organic light emitting diode was fabricated according to the same method as Element Example—1 except that ETL-1 was used in place of the compound 1-48 in Element Example—1, and evaluated. The obtained measurement results are shown in Table 4.

Element Reference Example—1

An organic light emitting diode was fabricated according to the same method as Element Example—1 except that ETL-2 described in Patent Document 1 was used in place of the compound 1-48 in Element Example—1, and evaluated. The obtained measurement results are shown in Table 4.

Element Reference Example—2

An organic light emitting diode was fabricated according to the same method as Element Example—1 except that ETL-3 described in Patent Document 1 was used in place of the compound 1-48 in Element Example—1, and evaluated. The obtained measurement results are shown in Table 4.

Element Reference Example—3

An organic light emitting diode was fabricated according to the same method as Element Example—1 except that ETL-4 described in Japanese Unexamined Patent Application, Publication No. 2017-105717 was used in place of the compound 1-48 in Element Example—1, and evaluated. The obtained measurement results are shown in Table 4.

TABLE 4

| | Compound | Driving voltage | Current efficiency |
|---|---|---|---|
| Element Example-1 | 1-48 | 98 | 104 |
| Element Comparative Example-1 | ETL-1 | 100 | 89 |
| Element Reference Example-1 | ETL-2 | 100 | 95 |
| Element Reference Example-2 | ETL-3 | 103 | 96 |
| Element Reference Example-3 | ETL-4 | 100 | 100 |

Figure 3:
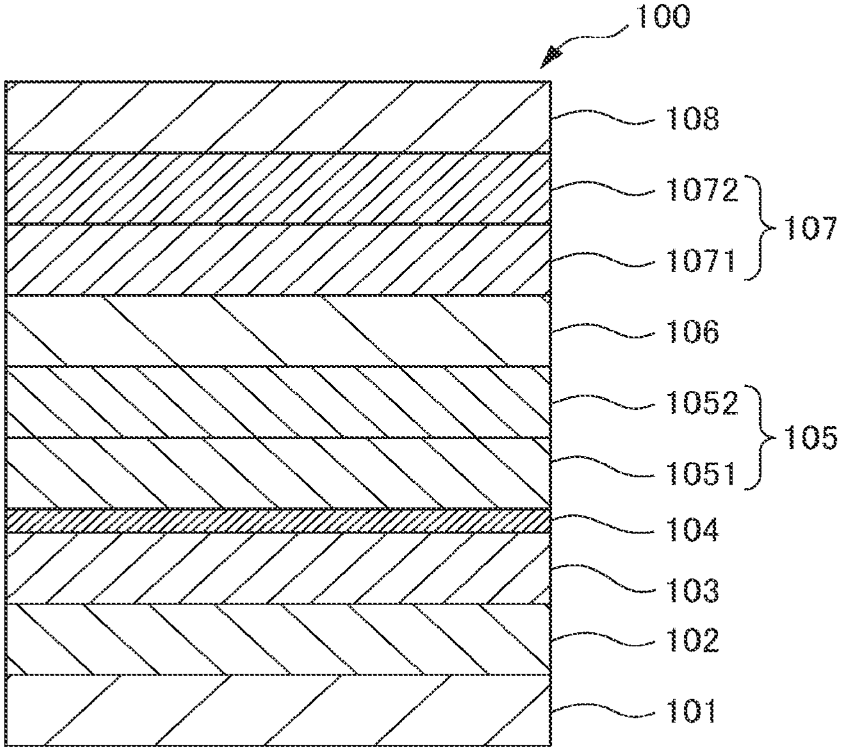
FIG. 3 is a schematic cross-sectional view showing an example of a layered structure (Element Example—2) of an organic light emitting diode containing a cyclic azine compound according to an aspect of the present disclosure.

Element Example—2 (See FIG. 3)

(Preparation of Substrate 101 and Anode 102)

As a substrate having an anode on the surface thereof, a glass substrate with an indium oxide-tin (ITO) transparent electrode formed of a 2 mm wide ITO film (film thickness: 110 nm) and patterned in stripes was prepared. Then, this substrate was cleaned with isopropyl alcohol, and thereafter surface-treated by ozone ultraviolet ray cleaning.

(Preparation of Vacuum Deposition)

Each layer was vacuum deposited on the cleaned and surface-treated substrate by vacuum deposition procedure to form and laminate the layers. First, the glass substrate was introduced to a vacuum deposition chamber, and the pressure within the vacuum deposition chamber was reduced to $1.0\times10^{-4}$ Pa. Then, the layers were fabricated in the following order according to the respective film formation conditions.

(Fabrication of Hole Injection Layer 103)

A hole injection layer 103 was fabricated by depositing sublimation-purified HIL at a rate of 0.15 nm/sec to achieve a film thickness of 50 nm.

(Fabrication of Charge Generation Layer 104)

A charge generation layer 104 was fabricated by depositing sublimation-purified HAT-CN at a rate of 0.15 nm/sec to achieve a film thickness of 5 nm.

(Fabrication of First Hole Transport Layer 1051)

A first hole transport layer 1051 was fabricated by depositing sublimation-purified HTL at a rate of 0.15 nm/sec to achieve a film thickness of 10 nm.

(Fabrication of Second Hole Transport Layer 1052)

A second hole transport layer 1052 was fabricated by depositing sublimation-purified EBL-2 at a rate of 0.15 nm/sec to achieve a film thickness of 5 nm.

(Fabrication of Light Emitting Layer 106)

A light emitting layer 106 was fabricated by depositing sublimation-purified BH-2 and BD-1 in a ratio of 95:5 (mass ratio) to achieve a film thickness of 25 nm. The film formation rate was 0.18 nm/sec.

(Fabrication of First Electron Transport Layer 1071)

A first electron transport layer 1071 was fabricated by depositing sublimation-purified HBL-2 at a rate of 0.05 nm/sec to achieve a film thickness of 5 nm.

(Fabrication of Second Electron Transport Layer 1072)

A second electron transport layer 1072 was fabricated by depositing the compound 1-48 and Liq in a ratio of 50:50 (mass ratio) to achieve a film thickness of 25 nm. The film formation rate was 0.15 nm/sec.

(Fabrication of Cathode 108)

Finally, a cathode 108 was formed using a metal mask placed so as to be perpendicular to the ITO stripes on the substrate. The cathode was formed by depositing silver/magnesium (mass ratio 1/10) and silver in this order to achieve a film thickness of 80 nm and 20 nm, respectively, and thus had a two-layer structure. The film formation rate for silver/magnesium was 0.5 nm/sec, and the film formation rate for silver was 0.2 nm/sec.

According to the procedure described above, an organic light emitting diode 100 having a light emission area of 4 $mm^2$, as shown in FIG. 3, was fabricated. It should be noted that the thickness of each layer was measured using a stylus profilometer (DEKTAK, manufactured by Bruker).

Furthermore, this element was encapsulated in a glove box under nitrogen atmosphere with an oxygen and moisture concentration of 1 ppm or less. The encapsulation was performed by encapsulating the deposition substrate (element) in a glass encapsulating cap using bisphenol F epoxy resin (manufactured by Nagase ChemteX Corporation).

Direct current was applied to the organic light emitting diode fabricated as described above, and light emission characteristics thereof was evaluated using a luminance meter (product name: BM-9, manufactured by Topcon Technohouse Corporation). Current efficiency (cd/A) under the application of a current density of 10 $mA/cm^2$ was measured as the light emission characteristics. It should be noted that the driving voltage shown below is a relative value with respect to the result of Element Reference Example 4 described below as a reference value (100). The obtained measurement results are shown in Table 5.

Element Example—3

An organic light emitting diode was fabricated according to the same method as Element Example—2 except that the compound 1-49 was used in place of the compound 1-48 in Element Example—2, and evaluated. The obtained measurement results are shown in Table 5.

Element Example—4

An organic light emitting diode was fabricated according to the same method as Element Example—2 except that the compound 1-50 synthesized in Synthesis Example—5 was used in place of the compound 1-48 in Element Example—2, and evaluated. The obtained measurement results are shown in Table 5.

Element Example—5

An organic light emitting diode was fabricated according to the same method as Element Example—2 except that the compound 1-51 synthesized in Synthesis Example—6 was used in place of the compound 1-48 in Element Example—2, and evaluated. The obtained measurement results are shown in Table 5.

Element Example—6

An organic light emitting diode was fabricated according to the same method as Element Example—2 except that the compound 1-52 was used in place of the compound 1-48 in Element Example—2, and evaluated. The obtained measurement results are shown in Table 5.

Element Example—7

An organic light emitting diode was fabricated according to the same method as Element Example—2 except that the compound 1-64 was used in place of the compound 1-48 in Element Example—2, and evaluated. The obtained measurement results are shown in Table 5.

Element Example—8

An organic light emitting diode was fabricated according to the same method as Element Example—2 except that the compound 1-65 was used in place of the compound 1-48 in Element Example—2, and evaluated. The obtained measurement results are shown in Table 5.

Element Reference Example—4

An organic light emitting diode was fabricated according to the same method as Element Example—2 except that ETL-4 described in Japanese Unexamined Patent Application, Publication No. 2017-105717 was used in place of the compound 1-48 in Element Example—2, and evaluated. The obtained measurement results are shown in Table 5.

TABLE 5

| | Compound | Driving voltage | Current efficiency |
|---|---|---|---|
| Element Example-2 | 1-48 | 98 | 110 |
| Element Example-3 | 1-49 | 99 | 115 |
| Element Example-4 | 1-50 | 97 | 101 |
| Element Example-5 | 1-51 | 97 | 106 |
| Element Example-6 | 1-52 | 96 | 104 |
| Element Example-7 | 1-64 | 97 | 109 |
| Element Example-8 | 1-65 | 97 | 110 |
| Element Reference Example-4 | ETL-4 | 100 | 100 |

Element Example—9

An organic light emitting diode was fabricated according to the same method as Element Example—1 except that EBL-4, BD-3 and the compound 1-67 were used in place of EBL-3, BD-2 and the compound 1-48 in Element Example—1, respectively, and a cathode was formed by depositing ytterbium, silver/magnesium (mass ratio 9/1) and silver in this order so achieve a film thickness of 2 nm, 12 nm and 90 nm, respectively, and thus had a three-layer structure, and evaluated. In this regard, the film formation rate for ytterbium was 0.02 nm/sec, the film formation rate for silver/magnesium was 0.5 nm/sec, and the film formation rate for silver was 0.2 nm/sec. The obtained measurement results are shown in Table 6.

Element Reference Example—5

An organic light emitting diode was fabricated according to the same method as Element Example—9 except that ETL-4 was used in place of the compound 1-67 in Element Example—9, and evaluated. The obtained measurement results are shown in Table 6.

TABLE 6

| | Compound | Driving voltage | Current efficiency |
|---|---|---|---|
| Element Example-9 | 1-67 | 98 | 104 |
| Element Reference Example-5 | ETL-4 | 100 | 100 |

Element Example—10

An organic light emitting diode was fabricated according to the same method as Element Example—1 except that EBL-4 and BD-3 were used in place of EBL-3 and BD-2 in Element Example—1, respectively, and a cathode was formed by depositing ytterbium, silver/magnesium (mass ratio 9/1) and silver in this order so achieve a film thickness of 2 nm, 12 nm and 90 nm, respectively, and thud had a three-layer structure, and evaluated. In this regard, the film formation rate for ytterbium was 0.02 nm/sec, the film formation rate for silver/magnesium was 0.5 nm/sec, and the film formation rate for silver was 0.2 nm/sec. The obtained measurement results are shown in Table 7.

Element Example—11

An organic light emitting diode was fabricated according to the same method as Element Example—10 except that the compound 1-66 was used in place of the compound 1-48 in Element Example—10, and evaluated. The obtained measurement results are shown in Table 7.

Element Example—12

An organic light emitting diode was fabricated according to the same method as Element Example—10 except that the compound 1-62 was used in place of the compound 1-48 in Element Example—10, and evaluated. The obtained measurement results are shown in Table 7.

Element Comparative Example—2

An organic light emitting diode was fabricated according to the same method as Element Example—10 except that ETL-1 was used in place of the compound 1-48 in Element Example—10, and evaluated. The obtained measurement results are shown in Table 7.

TABLE 7

| | Compound | Driving voltage | Current efficiency |
|---|---|---|---|
| Element Example-10 | 1-48 | 97 | 105 |
| Element Example-11 | 1-66 | 96 | 108 |
| Element Example-12 | 1-62 | 97 | 108 |
| Element Comparative Example-2 | ETL-1 | 100 | 100 |

Based on Tables 4 to 7, the cyclic azine compound (1) according to an aspect of the present disclosure can provide an organic light emitting diode exhibiting both excellent driving voltage characteristics and excellent current efficiency characteristics, as compared with the conventionally known cyclic azine compounds.

In addition, the cyclic azine compound (1) according to an aspect of the present disclosure is utilized as an electron transport material for an organic light emitting diode exhibiting both excellent driving voltage characteristics and excellent current efficiency characteristics. Furthermore, the cyclic azine compound (1) can provide an organic light emitting diode with lower power consumption.

Further, a thin film formed from the cyclic azine compound (1) according to an aspect of the present disclosure is excellent in electron transport performances, hole blocking performances, redox resistance, water resistance, oxygen resistance, electron injection properties, etc., and therefore is useful as a material for an organic light emitting diode, and useful as an electron transport material, a hole blocking material, a light emitting host material, etc. Especially, such a thin film is useful when used in an electron transport material.

Furthermore, the cyclic azine compound (1) according to an aspect of the present disclosure has a wide band-gap, and a high triplet excitation level. Therefore, the cyclic azine compound can be suitably used for not only conventional fluorescence element applications, but also phosphorescence elements and organic light emitting diodes utilizing the thermally activated delayed fluorescence (TADF).

While the present invention has been described in detail and with reference to specific embodiments, it is obvious to one of ordinary skill in the art that a variety of changes and modifications can be made to the specific embodiments without departing from the spirit and scope of the present invention. It should be noted that the entire contents of the specification, claims, drawings and abstract of Japanese patent application No. 2019-139746 filed on Jul. 30, 2019 are referred to herein and incorporated as the disclosure of the specification of the present invention.

EXPLANATION OF REFERENCE NUMERALS

1, 101 substrate
2, 102 anode
3, 103 hole injection layer
4, 104 charge generation layer
5, 105 hole transport layer
6, 106 light emitting layer
7, 107 electron transport layer
8, 108 cathode
51, 1051 first hole transport layer
52, 1052 second hole transport layer
71, 1071 first electron transport layer
72, 1072 second electron transport layer
100 organic light emitting diode

The invention claimed is:

1. A cyclic azine compound of formula (1):

(1)

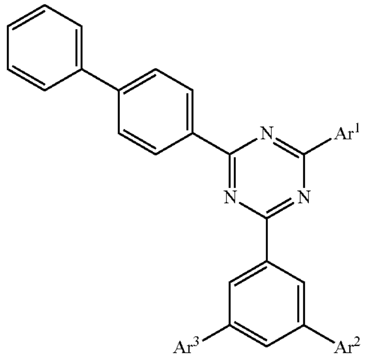

wherein $Ar^1$ is a phenyl group or a 4-biphenylyl group;

$Ar^2$ has one of formulas (2-1) to (2-3):

(2-1)

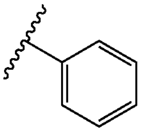

(2-2)

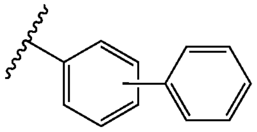

-continued (2-3)

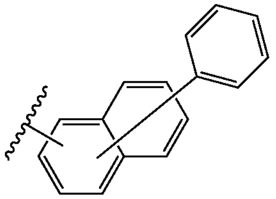

$Ar^3$ has one of formulas (3-2), (3-3), (3-5), (3-6), (3-7) and (3-9);

(3-2)

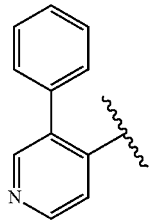

(3-3)

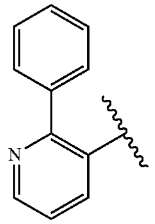

(3-5)

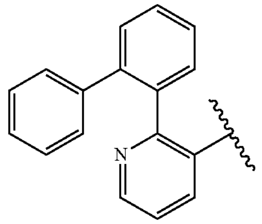

(3-6)

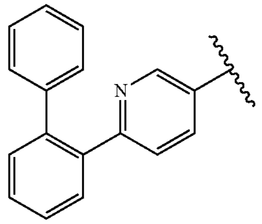

(3-7)

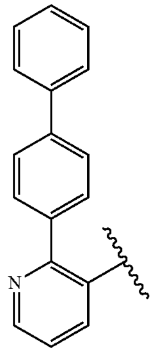

-continued
(3-9)
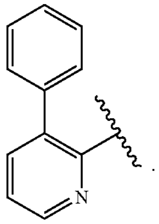
2. The cyclic azine compound according to claim 1, wherein
Ar$^2$ has one of formulas (2-1), (2-2a), (2-2b), (2-3a), and (2-3b)
(2-1)
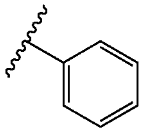
(2-2a)
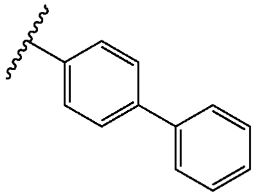
(2-2b)
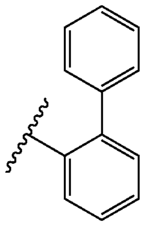
(2-3a)
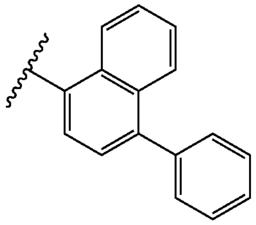
(2-3b)
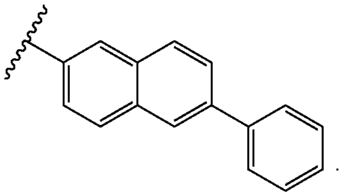
3. The cyclic azine compound according to claim 1, wherein Ar$^2$ has formula (2-2b)
(2-2b)
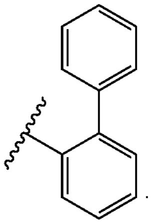
4. The cyclic azine compound according to claim 1, which has one of formulas (1-6), (1-15), (1-48), (1-51), (1-52), (1-54), (1-65), and (1-66):
1-6
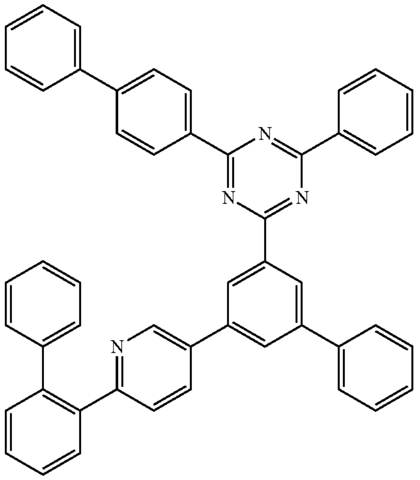
1-15
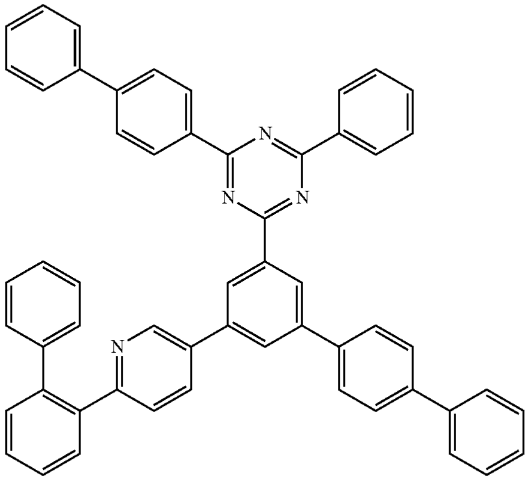

-continued 1-48

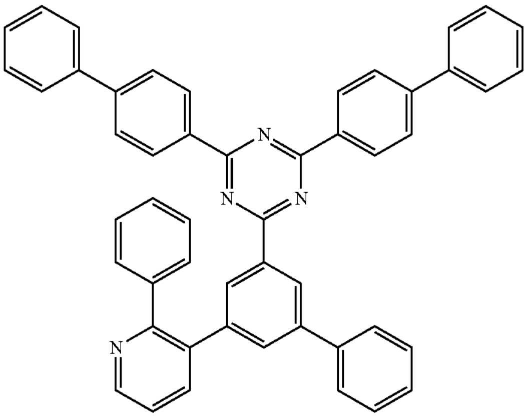

1-51

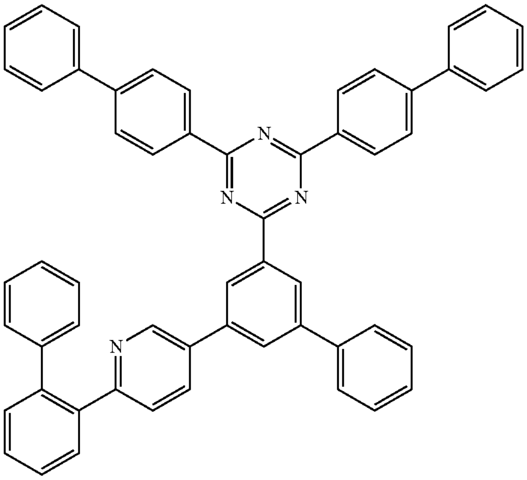

1-52

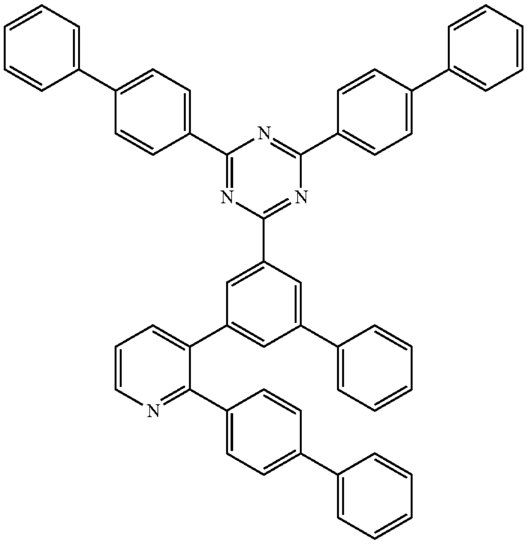

-continued 1-54

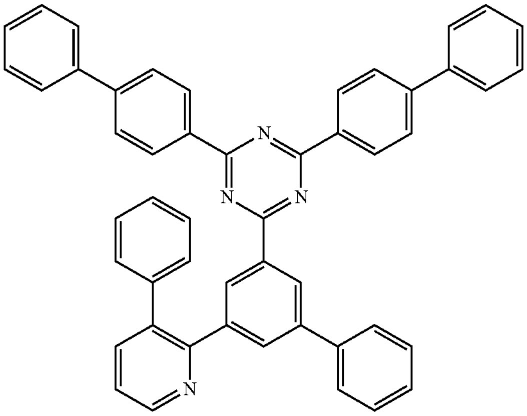

1-65

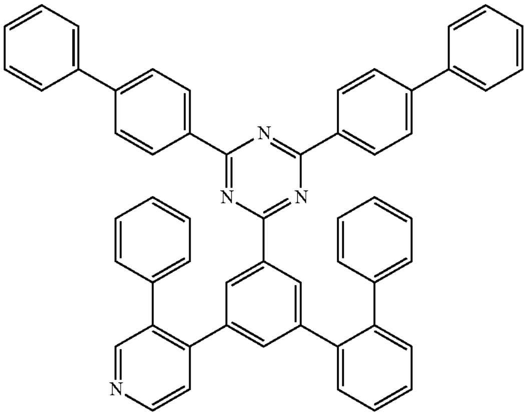

1-66

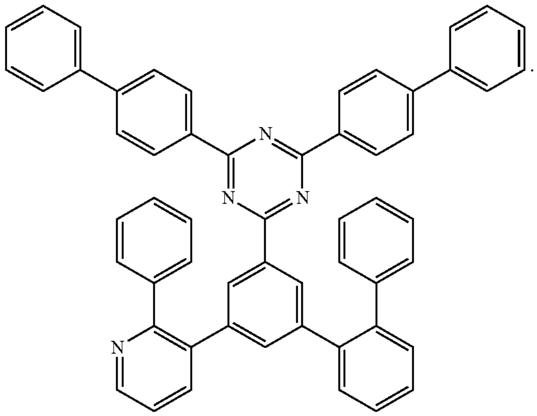

5. An organic light emitting diode, comprising:

an electron transport material comprising the cyclic azine compound of claim 1.

6. An organic light emitting diode, comprising:

an electron transport material comprising the cyclic azine compound of claim 2.

7. An organic light emitting diode, comprising:

an electron transport material comprising the cyclic azine compound of claim 3.

8. A method for producing a cyclic azine compound of formula (1), comprising:

reacting a compound of formula (4) with a compound of formula (3),

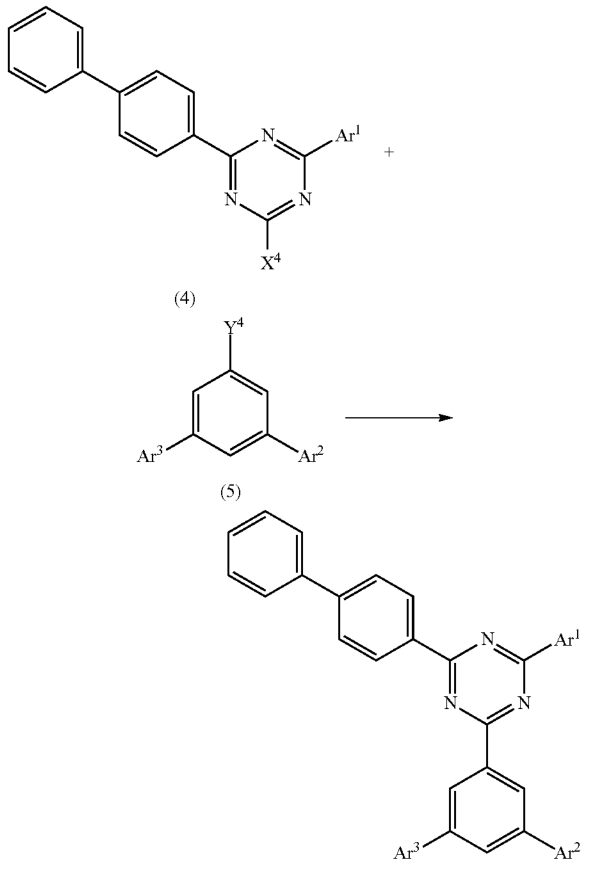
(4) (5) (1)
wherein
$Ar^1$ is a phenyl group or a 4-biphenylyl group;
$Ar^2$ has one of formulas (2-1) to (2-3):
(2-1)
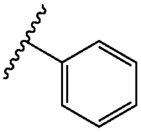
(2-2)
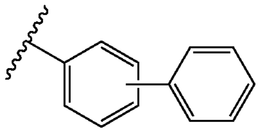
(2-3)
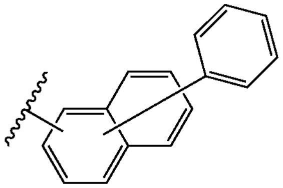
;
and
$Ar^3$ has one of formulas (3-2), (3-3), (3-5), (3-6), (3-7), and (3-9):
(3-2)
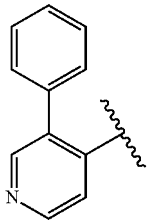
(3-3)
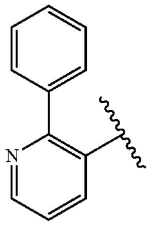
(3-5)
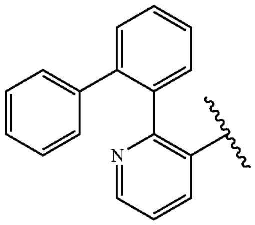
(3-6)
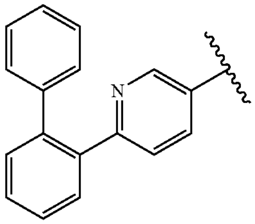
(3-7)
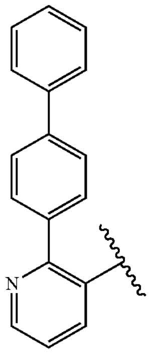
(3-9)
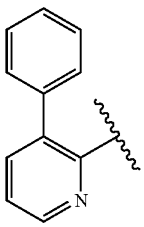
;
$X^4$ is a leaving group; and
$Y^4$ is a halogen atom, a metal-containing group, or a boron-containing group.

9. A pyridine compound of formula (5):
(5)
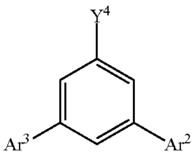
wherein
Ar$^2$ has one of formulas (2-1) to (2-3):
(2-1)
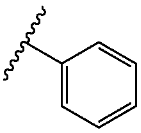
(2-2)
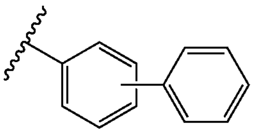
(2-3)
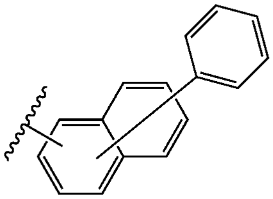
;
Ar$^3$ has one of formulas (3-2), (3-3), (3-5), (3-6), (3-7) and (3-9):
(3-2)
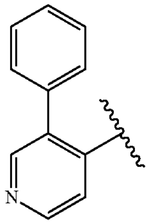
(3-3)
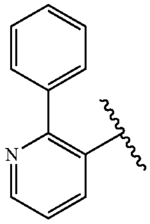
-continued
(3-5)
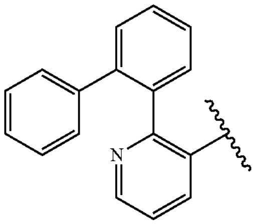
(3-6)
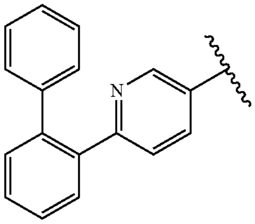
(3-7)
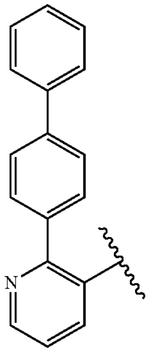
(3-9)
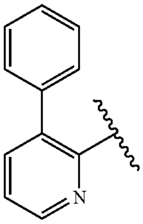
; and
Y$^4$ is a halogen atom, a metal-containing group, or a boron-containing group.
10. The pyridine compound according to claim 9, which has one of formulas (5-1), (5-2) or (5-3)
(5-1)
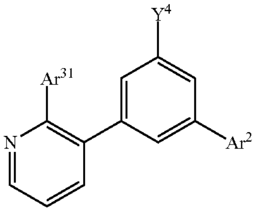

-continued
(5-2)
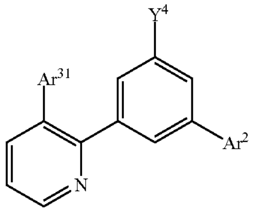
(5-3)
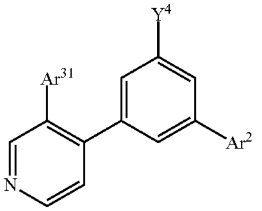
wherein
in formula (5-1), $Ar^{31}$ is selected from the group consisting of unsubstituted phenyl, unsubstituted 2-biphenylyl, and unsubstituted 4-biphenylyl,
in formula (5-2), $Ar^{31}$ is unsubstituted phenyl,
in formula (5-3), $Ar^{31}$ is unsubstituted phenyl, and
$Y^4$ and $Ar^2$ are as defined in claim 9.
* * * * *